(12) United States Patent
Baker, Jr. et al.

(10) Patent No.: US 8,912,323 B2
(45) Date of Patent: Dec. 16, 2014

(54) MULTIFUNCTIONAL SMALL MOLECULES

(75) Inventors: James R. Baker, Jr., Ann Arbor, MI (US); Hong Zong, Ann Arbor, MI (US); Thommey P. Thomas, Dexter, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 312 days.

(21) Appl. No.: 13/504,046

(22) PCT Filed: Sep. 30, 2010

(86) PCT No.: PCT/US2010/050893
§ 371 (c)(1),
(2), (4) Date: Jun. 25, 2012

(87) PCT Pub. No.: WO2011/059586
PCT Pub. Date: May 19, 2011

(65) Prior Publication Data
US 2012/0259114 A1   Oct. 11, 2012

Related U.S. Application Data

(60) Provisional application No. 61/256,699, filed on Oct. 30, 2009.

(51) Int. Cl.
| | | |
|---|---|---|
| C07D 251/28 | (2006.01) | |
| C07D 251/30 | (2006.01) | |
| C07D 251/48 | (2006.01) | |
| C07D 251/54 | (2006.01) | |
| C07D 403/14 | (2006.01) | |
| C07D 405/14 | (2006.01) | |
| A61K 31/53 | (2006.01) | |
| C08G 83/00 | (2006.01) | |
| A61K 47/48 | (2006.01) | |

(52) U.S. Cl.
CPC ........ C08G 83/003 (2013.01); A61K 47/48107 (2013.01); A61K 47/48207 (2013.01)
USPC ........... 544/180; 544/196; 544/204; 544/215; 514/241; 514/245

(58) Field of Classification Search
USPC ........... 544/180, 196, 204, 215; 514/241, 245
See application file for complete search history.

(56) References Cited

U.S. PATENT DOCUMENTS

| | | |
|---|---|---|
| 4,161,948 A | 7/1979 | Bichon |
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,708,930 A | 11/1987 | Kortright et al. |
| 4,713,975 A | 12/1987 | Tomalia et al. |
| 4,737,550 A | 4/1988 | Tomalia et al. |
| 4,743,543 A | 5/1988 | Kortright |
| 4,827,945 A | 5/1989 | Groman |
| 4,857,599 A | 8/1989 | Tomalia et al. |
| 4,871,779 A | 10/1989 | Killat et al. |
| 4,892,935 A | 1/1990 | Yoshida et al. |
| 4,914,021 A | 4/1990 | Toth |
| 4,918,164 A | 4/1990 | Hellstrom et al. |
| 4,921,789 A | 5/1990 | Salem et al. |
| 4,921,790 A | 5/1990 | O'Brien |
| 4,939,240 A | 7/1990 | Chu et al. |
| 4,946,778 A | 8/1990 | Ladner et al. |
| 4,963,484 A | 10/1990 | Kufe |
| 4,965,128 A | 10/1990 | Greidanus |
| 5,041,516 A | 8/1991 | Frechet et al. |
| 5,053,489 A | 10/1991 | Kufe |
| 5,110,911 A | 5/1992 | Samuel et al. |
| 5,270,163 A | 12/1993 | Gold et al. |
| 5,338,532 A | 8/1994 | Tomalia et al. |
| 5,354,308 A | 10/1994 | Simon et al. |
| 5,387,617 A | 2/1995 | Hedstrand et al. |
| 5,393,795 A | 2/1995 | Hedstrand et al. |
| 5,393,797 A | 2/1995 | Hedstrand et al. |
| 5,475,096 A | 12/1995 | Gold et al. |
| 5,512,443 A | 4/1996 | Schlom et al. |
| 5,527,524 A | 6/1996 | Tomalia et al. |
| 5,545,530 A | 8/1996 | Satomura et al. |
| 5,560,929 A | 10/1996 | Hedstrand et al. |
| 5,631,329 A | 5/1997 | Yin et al. |
| 5,661,025 A | 8/1997 | Szoka et al. |

(Continued)

FOREIGN PATENT DOCUMENTS

| | | |
|---|---|---|
| CA | 2187921 | 11/1995 |
| CA | 2386998 | 4/2001 |

(Continued)

OTHER PUBLICATIONS

Wangler, C., et al., "Antibody-dendrimer conjugates: the number, not the size of the dendrimers, determines the immunoreactivity," Bioconjug Chem., Apr. 2008, vol. 19(4), pp. 813-820.

Dirks, A. (Ton) J., et al., "Monitoring Protein—Polymer Conugation by a Fluorogenic (Cu(I)-Catalyzed Azide—Alkyne 1,3-Dipolar Cycloaddition," Bioconjugate Chemistry, vol. 20, No. 6, pp. 1129-1138 (Jun. 2009).

Lalwani, Sanjiv, et al., "Mimicking PAMAM Dendrimers with Amphoteric, Hybrid Triazine Dendrimers: A Comparison of Dispersity and Stability," Macromolecules, vol. 42, No. 17, pp. 6723-6732 (Aug. 12, 2009).

Rheumatoid arthiritis, Merck Manual Home Ed. Avaialble at http://wwww.merckmanuals.com/home/print/sec05/ch066/ch066b.html (printed Apr. 19, 2011).

Levi-Montalcini, "The Nerve Growth Factor Thirty-Five Years Later," In Vitro Cell., Devi. Biol. 23:227 (1987).

Liao, et al., "Chromophore-assisted laser inactivation of proteins is mediated by the photogeneration of free radicals," PNAS 91:2659 (1994).

(Continued)

Primary Examiner — Venkataraman Balasubramanian
(74) Attorney, Agent, or Firm — Casimir Jones SC

(57) ABSTRACT

The present invention relates to dendrimer synthesis. Specifically, the present invention relates to triazine scaffolds capable of click chemistry for one-step synthesis of functionalized dendrimers, and methods of making and using the same.

11 Claims, 10 Drawing Sheets

(56) References Cited

U.S. PATENT DOCUMENTS

| | | |
|---|---|---|
| 5,674,192 A | 10/1997 | Sahatjian |
| 5,693,014 A | 12/1997 | Abele et al. |
| 5,693,763 A | 12/1997 | Codington et al. |
| 5,714,166 A | 2/1998 | Tomalia et al. |
| 5,733,303 A | 3/1998 | Israel |
| 5,755,722 A | 5/1998 | Barry |
| 5,773,527 A | 6/1998 | Tomalia et al. |
| 5,792,105 A | 8/1998 | Lin |
| 5,795,582 A | 8/1998 | Wright |
| 5,800,391 A | 9/1998 | Kontos |
| 5,800,508 A | 9/1998 | Goicoechea et al. |
| 5,800,519 A | 9/1998 | Sandock |
| 5,808,005 A | 9/1998 | Codington et al. |
| 5,843,089 A | 12/1998 | Sahatjian |
| 5,851,228 A | 12/1998 | Pinheiro |
| 5,855,866 A | 1/1999 | Thorpe |
| 5,855,881 A | 1/1999 | Loike et al. |
| 5,857,998 A | 1/1999 | Barry |
| 5,861,319 A | 1/1999 | Lin |
| 5,866,561 A | 2/1999 | Ungs |
| 5,868,719 A | 2/1999 | Tsukernik |
| 5,876,445 A | 3/1999 | Andersen |
| 5,892,019 A | 4/1999 | Schlom |
| 5,892,020 A | 4/1999 | Mezes |
| 5,898,005 A | 4/1999 | Singh |
| 5,902,863 A | 5/1999 | Dvornic et al. |
| 5,908,413 A | 6/1999 | Lange |
| 5,913,894 A | 6/1999 | Schmitt |
| 5,922,887 A | 7/1999 | Dondio et al. |
| 5,933,145 A | 8/1999 | Meek |
| 5,935,114 A | 8/1999 | Jang |
| 6,051,429 A | 4/2000 | Hawley-Nelson et al. |
| 6,054,444 A | 4/2000 | Jackson |
| 6,267,987 B1 | 7/2001 | Park et al. |
| 6,312,679 B1 | 11/2001 | Tomalia et al. |
| 6,471,968 B1 | 10/2002 | Baker et al. |
| 6,485,718 B1 | 11/2002 | Parthasarathy |
| 6,585,956 B2 | 7/2003 | Malik et al. |
| 6,869,772 B2 | 3/2005 | Lichtman et al. |
| 7,078,461 B2 | 7/2006 | Tomalia et al. |
| 7,097,856 B2 | 8/2006 | Frechet |
| 7,208,486 B2 | 4/2007 | Burnett |
| 7,261,875 B2 | 8/2007 | Li |
| 7,368,512 B2 | 5/2008 | Newkome |
| 7,419,686 B2 | 9/2008 | Kaiko et al. |
| 7,459,145 B2 | 12/2008 | Bao |
| 7,572,459 B2 | 8/2009 | Matthews et al. |
| 7,745,229 B2 | 6/2010 | Wang |
| 8,252,834 B2 * | 8/2012 | Baker et al. ............... 514/412 |
| 2001/0031498 A1 | 10/2001 | Leclercq |
| 2002/0165179 A1 | 11/2002 | Baker, Jr. |
| 2003/0180250 A1 | 9/2003 | Chauhan et al. |
| 2004/0109842 A1 | 6/2004 | Baker, Jr. |
| 2004/0120979 A1 | 6/2004 | Roessler et al. |
| 2005/0214247 A1 | 9/2005 | Shaunak |
| 2006/0057211 A1 | 3/2006 | Chorny |
| 2007/0020620 A1 | 1/2007 | Finn |
| 2007/0041934 A1 | 2/2007 | Williams |
| 2007/0298006 A1 | 12/2007 | Tomalia et al. |
| 2008/0045689 A1 | 2/2008 | Stumbe et al. |
| 2008/0171067 A1 | 7/2008 | Govindan et al. |
| 2008/0200562 A1 | 8/2008 | Yin |
| 2008/0312344 A1 | 12/2008 | Liskamp et al. |
| 2009/0012035 A1 | 1/2009 | Jacobson et al. |
| 2009/0053139 A1 | 2/2009 | Shi |
| 2009/0069561 A1 | 3/2009 | Fokin et al. |
| 2009/0082537 A1 | 3/2009 | Hernandez et al. |
| 2009/0088376 A1 | 4/2009 | Baker, Jr. |
| 2009/0104119 A1 | 4/2009 | Majoros et al. |
| 2009/0208580 A1 | 8/2009 | Shi |
| 2009/0287005 A1 | 11/2009 | Baker, Jr. |
| 2010/0136614 A1 | 6/2010 | Luo et al. |
| 2010/0158850 A1 | 6/2010 | Baker, Jr. |
| 2010/0160299 A1 | 6/2010 | Baker, Jr. |
| 2010/0183749 A1 | 7/2010 | Brey |

FOREIGN PATENT DOCUMENTS

| | | |
|---|---|---|
| CN | 101267803 | 9/2008 |
| EP | 0099758 | 10/1984 |
| EP | 0271180 | 6/1988 |
| EP | 1941861 | 7/2008 |
| JP | 2002-265495 | 9/2002 |
| WO | 88/01178 | 2/1988 |
| WO | 88/01180 | 2/1988 |
| WO | 90/02545 | 3/1990 |
| WO | 95/24221 | 9/1995 |
| WO | 95/28641 | 10/1995 |
| WO | 9707398 | 2/1997 |
| WO | 97/38134 | 10/1997 |
| WO | 98/33941 | 8/1998 |
| WO | 99/02651 | 1/1999 |
| WO | 99/07724 | 2/1999 |
| WO | 9961662 | 2/1999 |
| WO | 99/10362 | 3/1999 |
| WO | 99/58656 | 11/1999 |
| WO | 00/16807 | 3/2000 |
| WO | 01/87348 | 11/2001 |
| WO | 0102861 | 11/2001 |
| WO | 03/003975 | 1/2003 |
| WO | 03/011115 | 2/2003 |
| WO | 03/055935 | 7/2003 |
| WO | 2006/033766 | 3/2006 |
| WO | 2007/011967 | 1/2007 |
| WO | 07012001 | 1/2007 |
| WO | 2007/034750 | 3/2007 |
| WO | 2007/080114 | 7/2007 |
| WO | 2008/008483 | 1/2008 |
| WO | 2011002852 | 1/2011 |
| WO | 2011028334 | 3/2011 |
| WO | 2011053618 | 5/2011 |
| WO | 20111059609 | 5/2011 |
| WO | 2011/072290 | 6/2011 |

OTHER PUBLICATIONS

Luck et al., "Plasma protein adsorption on biodegradable microspheres . . ." J. Control. Rel 55:107 (1998).

Madihally and Matthew, "Porous chitosan scaffolds for tissue engineering," Biomaterials 20(12):1133 (1999).

Majoros and Tomalia, Mar. 18, 2006 Abstract Only printed Apr. 20, 2009, "Synthesis and Characterization of Novel POPAM-PAMAM (POMAM) Hybrid Dendrimers as Reactive Modules for Nanodevice Construction" Eight Foresight Conference on Molecular Nanotechnology.

Majoros et al., "PAMAM Dendrimer-based multifunctional conjugate for cancer therapy: synthesis, characterization and functionality," Biomacromolecules, 2006, vol. 7, pp. 572-579.

Majoros, et al., "Acetylation of Poly(amidoamine) Dendrimers," Macromolecules 2003, 36, 5526-5529.

Malik et al., "A PAMAM Dendrimer-Platinate," Proc. Int'l Symp. Control. Rel. Bioact. Mater, 24:107 (1997).

Malik et al., "Dendrimers: Relationshipo between structure and biocompatibility in vitro, and preliminary studies on the biodistribution of (125)I-labelled polyamidoamine dendrimers in vivo," Journal of Controlled Relief 65:133-148 (2000).

Marlin et al., "A soluble form of intercellular adhesion molecule-1 inhibits rhinovirus infection," Nature 344:70 (1990).

Mayer et al., "Matrices for tissue engineering-scaffold structure for a bioartificial liver support system," J. Controlled Release 64(1-3):81 (2000).

Mendelsohn et al., "Cellular Receptor for Poliovirus: Molecular Cloning, . . ." Cell 56:855 (1989).

Monsigny et al., "Characterization and biological implications of membrane lectins in tumor, lymphoid and myeloid cells," Biochemie 70:1633 (1988).

Mosmann, "Rapid Colorimetric Assay for Cellular Growth and Survival: Application to Proliferation and Cytotoxity Assays," J. Immunol. Meth, 65:55 (1983).

Murphy, et al., "Photolytic Release of Nitric Oxide Modulates NMDA Receptor-mediated Transmission but Does not Induce Long-term Potentiation at Hippocampal Synapses," Neuropharm. 33:1375-85 (1994).

(56) References Cited

OTHER PUBLICATIONS

Naylor et al., Starburst Dendrimers. 5. Molecular Shape Control, J. Am. Chem. Soc. 111:2339-2341 (1989).
Niemiec et al., "Perifollicular Transgenic Expression of Human Interleukin-1 Rectpro Antagonist Protein following Topical Application of Novel Liposome-Plasmid DNA Formulations in Vivo," J. Pharm Sci. 86:701 (1997).
Orentas et al., "Detection of Epstein-Barr virus EBER sequence in post-transplant lymphoma patients with DNA dendrimers," Journal of Virological Methods 77:153-163 (1999).
Ottl, et al., "Preparation and Photoactivation of Caged Fluorophores and Caged Proteins Using a New Class of Heterobifunctional, Photocleavable Cross-Linking Reagents," Bioconjugate Chem. 9:143 (1998).
Page and Roy, "Synthesis and Biological Properties of Mannosylated Starburst Poly(amidoamine) Dendrimers," Bioconjugate Chem., 8:714 (1997).
Pan, et al., "Dendrimer modified magnetite nanoparticles for protein immobilization," Journal of Colloid and Interface Science, 2005, vol. 284, pp. 1-6.
Pandey, et al., "Chlorin and Porphyrine Derivatives as Potential Photosensitizers in Photodynamic Therapy," Photochem., Photobiol., 53:65-72 (1991).
Park et al., "Anti-HER2 immunoliposomes for targeted therapy of human tumors," Cancer Lett., 118:153 (1997).
Pasani et al., "Antitumor Complexes of Platinum with Carrier Molecules," Inorg. Chim. Acta 80:99 (1983).
Pavlova et al., "Biocompatible and biodegradable polyurethane polymers," Biomaterials 14(13):1024 (1993).
Pegrarn et al., Proc. Am. Soc. Clin. Oncol. 14:106 (1995).
Penault-Llorca et al., "Expression of FGF and FGF Receptor Genes in Human Breast Cancer," Int. J. Cancer 61:170 (1995).
Pillai V.N.R., "Photoremovable Protecting Groups in Organic Synthesis," Synthesis: 1-26 (1980).
Pratap Singh, "Terminal Groups in Starburst Dendrimers: Activation and Reaction with Proteins", 1998 Bioconnugate Chem. 9:54-63.
Press et al., "Expression of the HER-2/neu proto-oncogene in normal human adult and fetal tissues," Oncogene 5:953 (1990).
Quintana, et al., "Design and Function of a Dendrimer-Based Therapeutic Nanodevice Targeted to Tumor Cells Through the Folate Receptor," Pharmaceutical Research, vol. 19, No. 9, Sep. 2002.
Raczka et al., "The effect of synthetic surfactant Exosurf on gene transfer in mouse lung in vivo," Gene Ther 5:1333 (1998).
Riley, "Wound Healing," Am Fam. Physician 24:107 (1981).
Rinberg "Pnuematic capillary gun for ballistic delivery of microparticles" 2005 Applied Physics Letters vol. 87 pp. 1-3.
Roberts, et al., "Preliminary biological evaluation of oplyamidoamine (PAMAM) Starburst dendrimers," J. Biomed Mater res 30:53 (1996).
Roessler et al., "Substituted β-Cyclodextrins Interact with PAMAM Dendrimer-DNA Complexes and Modify Transfection Efficiency," Biochem. 124-129 (2001).
Ruff, et al., "CD4 receptor binding peptides that block HIV infectivity cause human monocyte chemotaxis," FEBS Letters 211:17 (1987).
Ruponen et al., "Interactions of polymeric and liposomal gene delivery systems with extracellular glycosaminoglycans: physicochemical and transfection studies," Biochmica ET Biophysica Acta 1415:331-341 (1999).
Sacerdote et al., "Vasoactive Intestinal Peptide 1-12: . . . " J. of Neuroscience Research 18:102 (1987).
Schneider, et al., "Distance-dependent fluorescence quenching on gold nanoparticles ensheathed with layer-by-layer assembled polyelectrolytes," Nano Letters, 2006, vol. 6, pp. 530-536.
Segura and Shea, "Materials for Non-Viral Gene Delivery" 2001 Annual Review of Materials Research, vol. 31 pp. 25-46.
Selman et al., "Copper Benzochlorin, a Novel Photosensitizer for Photodynamic Therapy . . . " Photochem. Photobio, 57:681-85 (1993).
Sessler et al., "Tripyrroledimethine-derived ("texaphyrine"-type) . . . " Proc. SPIE, 1426:318-29 (1991).
Sharon and Lis, "Lectins as Cell Recognition Molecules," Science 246:227 (1989).
Shchepinov et al., "Oligonucleotide dendrimers: synthesis and use as polylabelled DNA probes," Nucleic Acids Research 25:4447-4454 (1997).
Shea, "DNA delivery from polymer matrices for tissue engineering," Jun. 1999, Nature Biotechnology.
Shephey et al., "Monoclonal antibody identificaiton ofa 100-kDa membrane protein in HeLa cells and human spinal cord involved in poliovirus attachment," Proc. Natl. Acad. Sci. 85:7743 (1988).
Shortreed, et al., "Directed Energy Transfer Funnels in Dendrimetric Antenna Supermolecules," J. Phys. Chem. 101-6318 (1997).
Singh et al., "Starburst Dendrimers: Enhanced Performance and Flexibility for Immunoassays," Clin. Chem. 40:1845 (1994).
Sooklal, "A Blue-Emitting CdS/Dendrimer Nanocomposite," Adv. Mater, 10:1083 (1998).
Damen, E.W.P., et al., Biorganic & Medicinal Chemistry (2002) 10(1), pp. 71-77.
Hay, M.P., et al., Journal of Medicinal Chemistry (2003) 46(25), pp. 5533-5545.
Hay, M.P., et al., Journal of the Chemical Society-Perkin Transactions 1 (1999 (19), pp. 2759-2770.
Daniels, T.R., et al., Clinical Immunology (2006) 121(2), pp. 144-176.
Smith, M.W., and m. Gumbleton, Journal of Drug Targeting (2006) 14(4), pp. 191-214.
Koch, 1990, Angew. Chem. Int. Ed. Engl., 29:183-5.
Tomalia, et al., Chem. Int. Ed. Engl. 29:5305 (1990).
Yin, et al., J. Am. Chem. Soc., 120:2678 (1998).
Carelli, V., et al., Bioorganic & Medicinal Chemistry Letters (2003) 13(21), pp. 3765-3769.
Christrup, L.L., et al., International Journal of Pharmaceutics (1997). 154(2): pp. 157-165.
Drustrup, J., et al., International Journal of Pharmaceutics (1991), 71(1-2), pp. 105-116.
Groth, L., et al., International Journal of Pharmaceutics (1997) 154(2), pp. 149-155.
Mignat, C., et al., Journal of Pharmaceutical Sciences (1996) 85(7), pp. 690-694.
Hay, M.P., W.R. Wilson and W.A. Denny, Tetrahedron (2000) 56(4):, pp. 645-657.
de Groot, F.M.H., E.W.P. Damen, and H.W. Scheeren, Curr. Med. Chem.—Anti-Cancer Agents (2001) 8, pp. 1093-1122.
Dubowchik, G.M., and M.A. Walker, Pharmacology & Therapeutics (1999) 83, pp. 67-123.
Papot, S., et al., 2002, "Design of selectively activated anticancer prodrugs: elimination and cyclization strategies.", Curr Med Chem Anticancer Agents.; 2(2):155-85.
De Groot, F.M.H., et al., J. Org. Chem., 2001. 66, pp. 8815-8830.
Greenwald, R.B., et al., J. Med. Chem. (1999). 42: pp. 3657-3667.
Greenwald, R.B., et al., Bioconjugate Chem. (2003) 14, pp. 395-403.
Zhang, Z., et al., Pharmaceutical Research (2005) 22, pp. 381-389.
Antczak, C., et al., Bioorg. & Med. Chem (2001), 9: pp. 2843-2848.
Pohl, T., and H. Waldmann, J. Am. Chem. Soc. (1997), 119, pp. 6702-6710.
Sauerbrei, B., V. Jungmann, and -I. Waldmann, Angew. Chem. Int. Ed. (1998), 37: pp. 1143-1146.
Leung, L.Y. and T.A. Baillie, J. Med. Chem. (1986), 29, pp. 2396-2399.
Woolf, T., et al., J. Org. Chem. (1984) 49. pp. 3305-3310.
Nudelman, A., R.J. McCaully and S.C. Bell, J. Pharm. Sci. (1974) 63, pp. 1880-1885.
Esfand, R. and D.A. Tomalila, Drug Discovery Today (2001). 6, pp. 427-436.
Jansen, J.F.G.A., E.M.M. de Brabander van den Berg and E.W. Maijer, Science (1994). 266, pp. 1226-1229.
Kolhe, P., et al., International Journal of Pharmaceutics (2003), 259, pp. 143-160.
Man, N., et al., European Journal of Medicinal Chemistry (2006), 41, pp. 670-674.

(56) References Cited

OTHER PUBLICATIONS

Morgan, M.T., et al., J. Am. Chem., Soc. (2003), 125(50): pp. 15485-15489.
Papagiannaros, A., et al., International Journal of Pharmaceutics (2005), 302, pp. 29-38.
Patri, A.K., J.F. Kukowska-Latallo, and J.R. Baker, Advanced Drug Delivery Reviews (2005) 57(15), pp. 2203-2214.
Patri, A.K., I.J Majoros and J.R. Baker Jr., Current Opinion in Chemical Biology (2002) 6, pp. 466-471.
Qiu, L.Y., and Y.H. Bae, Pharmaceutical Research (2006) 23, p. 1-30.
Schcharbin, D. and B.M., Biochmica et Biophysica Acta (2006) 1760, pp. 1021-1026.
Shi, X., et al., Electrophoresis (2006) 27(9), pp. 1758-1767.
Islam, M.T., I.J., Majoros and J.R. Baker, Journal of Chromatography B-Analytical Technologies in the Biomedical and Life Sciences (2005) 822(1-2): p. 21-26).
Islam, Mt., et al., Analytical Chemistry (2005) 77(7): p. 2063-2070.
Shi, X., et al., Polymer (2005) 46: p. 3022-3034.
Shi, X., et al. Colloids Surf., A., (2006), 272, pp. 139-150.
Shi, X., I.J, Majoros and J.R. Baker, Jr., Mol. Pharm (2005), 2, pp. 278-294.
Shi, X.Y., et al., Electrophoresis (2005) 26(15), pp. 2949-2959.
Shi, X.Y., et al., Analysis (2006) 131(7): p. 842-848.
Shi, X.Y., et al. Analysis (2006) 131(3), pp. 374-381.
Shi, X.Y., et al. Electrophoresis (2005) 26(15): pp. 2960-2967.
Kuracka, L., et al., Clinical Chemistry (1996) 42(5), pp. 756-760.
Orlovic, D., et al., Chromatographia (2000) 52(11/12), pp. 732-734.
Svensson, J., et al., Journal of Chromatography B: Biomedical Sciences and Applications (1982), 230(2), pp. 427-432.
Hong, S., et al., Chemistry & Biology (2007), 14 (1), pp. 105-113.
Mammen, M., et al., Angewandte Chemie-International Edition (1998), 37 (20), pp. 2755-2794.
Hong, S.P., et al., Bioconjugate Chmistry (2004) 15, (4), pp. 774-782.
Svenson, S., et al., Advanced Drug Delivery Reviews (2005), 57 (15), pp. 2106-2129.
Hong, S.P., et al., Bioconjugate Chmistry (2006) 17(3), pp. 728-734.
Leroueil, P.R., Acc. Chem. Res. 40(5) (2007) pp. 335-342.
Thomas, T.P., et al., Biomacromoledules (2004) 5, (6) pp. 2269-2274.
Shukla, R., et al., Bioconjugate Chemistry (2006), 17 (5), pp. 1109-1115.
Wu, G., et al., Molecular Cancer Therapeutics (2006) 5(1) pp. 52-59.
Wu, G., et al., Bioconjugate Chemistry (2004) 15(1), pp. 185-194.
Backer, M.V., et al., Molecular Cancer Therapeutics (2005) 4(9), pp. 1423-1429.
Shukla, R., et al., Chemical Communications (2005) 46, pp. 5739-5741.
Sheng, K.C., et al., European Journal of Immunology (2008), 38, pp. 424-436.
Baek, M.G., et al., Bioorganic & Medicinal Chemistry (2002) 10 (1) pp. 11-17.
Taite, L.J, et al., Journal of Biomaterials Science-Polymer Edition (2006) 17(10), pp. 1159-1172.
Kono, K., et al., Bioconjugate Chemistry (1999) 10(6), pp. 1115-1121.
Shukla, S., et al., Bioconjugate Chemistry (2003) 14(1), pp. 158-167.
Thomas, t.p., et al., Journal of Medicinal Chemistry (2005), 48 (11), pp. 3729-3735.
Myc, A., et al., Anti-Cancer Drugs (2008) 19, pp. 143-149.
Majoros, I.J., et al., Journal of Medicinal Chmistry (2005) 48 (19) pp. 5892-5899.
Kukowska-Latallo, J.F., et al., Cancer Research (2005) 65(12) pp. 5317-5324.
Myc, a., et al., Biomacromolecules (2007) 8, pp. 2986-2989.
Myc, A., et al., Biomacromolcules (2007) 8 (1), pp. 13-18.
Landmark, K.J., et al., ACS Nano (2008) 2 (4), pp. 773-783.
Mullen, D.G., Bioconjug. Chem. 19(9) (2008) pp. 1748-1752.
Choi, Y., Nanostructured Supramolecular Arrays Based on Dendrimers Using DNA: Desgin, Synthesis and Biological Evaluation. Biomed. Eng. (NY), vol. Ph.D., Dissertation, University of Michigan, Ann Arbor, Mi (2005), p. 191.
Lee, J.W., Macromolecules 39(6) (2006), pp. 2418-2422.
Wu, P., Chem. Commun. (46) (2005), pp. 5775-5777.
Goyal, P., Chem. Eur. J. 13 (2007), pp. 8801-8810.
Yoon, K., Org. Letter 9(11) (2007), pp. 2051-2054.
Choi, Y.S., et al., Nano Letter 4(3) (2004), pp. 391-397.
Demattie, C.R., et al., Nano Letters 4(5) (2004), pp. 771-777.
Choi, Y., et al., Chem. Biol. 12(1) (2005), pp. 35-43.
Rostovtsev, V.V., et al., Angewandte Chemie-Inernational Edition (2002) 41 (14), p. 2596.
Wu, P., et al., Angewandte Chemie-International Edition (2004) 43 (30) pp. 3928-3932.
Wu, P., et al., Aldrichimica Acta 40(1) (2007), pp. 7-17.
Lee, J.W., et al., Bioconjugate Chemistry (2007) 18(2), pp. 579-584.
Lee, J.W., et al., Journal of Polymer Science Part a-Pollymer Chemistry (2008) 46, pp. 1083-1097.
Lee, J.W., et al., Tetrahedron (2006) 62(5), pp. 894-900.
Hoffman, R.E., Magn. Reson. Chem. (2006), 44, pp. 606-616.
De Groot, Franciscus, M.H., "Cascade-Release Dendrimers, Liberate All End Groups Upon a Single Triggering Event in the Dendritic Core," Angew. Chem. Int. Ed. (2003), vol. 42, pp. 4490-4494.
Lee, Cameron C., et al., "Designing Dendrimers for Biological Applications, Nature Biotechnology," Dec. 2005, vol. 23, No. 12, pp. 1517-1526.
Bloodworth, D., Phys. Med. Rehabil Clin. N. Am., (2006) 17(2), pp. 355-379.
Liu, J.K., et al., Neurobiology of Disease (2005) 1993), pp. 407-418.
Beall, H.D., et al., Journal of Medicinal Chemistry (1998) 41(24), pp. 4755-4766.
Ferrer, S., D.P. Naughton and M.D. Threadgill, Tetrahedron (2003) 59(19), pp. 3445-3454.
Naylor, M.A., et al., Journal of Medicinal Chemistry (1997) 40(15), pp. 2335-2346.
Zhang, Z., et al., Organic & Biomolecular Chemistry (2005) 3(10), pp. 1905-1910.
Phillips, R.M., et al., Journal of Medicinal Chemistry (1999) 42(20), pp. 4071-4080.
Frechet, Jean M.J., et al., "Reversed-phase high-performance liquid chromatographyj of functionalized dendritic macromolecules," Journal of Chromatography A, 667 (1994), pp. 284-289.
Mullen, et al., "Design, synthesis, and biological functionality of a dendrimer-based modular drug delivery platform," Bioconjugate Chemistry, vol. 22, No. 4, pp. 679-689 (Mar. 22, 2011).
Opsteen, et al., "Modular synthesis of block copolymers via cycloaddition of terminal azide and alkyne functionalized polymers", Chemical Communicaitons, vol. 1, pp. 57-59 (2005).
Yim, et al., "Versatile conjugation of octreotide to dendrimers by cycloaddition ("Click") chemistry to yield high-affinity mulivalent cyclic peptide dendrimers," Bioconjugate Chemistry, vol. 20, No. 7, pp. 1323-1331 (2009).
Wang, et al., "Synthesis and Application of Carbohydrate-Containing Polymers", Chem. Mater. (2002) 14, pp. 3232-3244.
Abel et al., "The Selective Concentration of Sulpha-diazine and Related Compounds in Malignant Tissue," Eur. J. Cancer 9:4 (1973).
Abrams, et al., "Programmed cell death during Drosophila embryogenesis," Development 117:29 (1993).
Adlish et al., "Identification of a Putative Cell Receptor for Human Cytomegalovirus," Virology 176:337 (1990).
Akutsu, et al., "Schedule-dependent Interaction Between Paclitaxel and Doxorubicin in Human Cancer Cell Lines in Vitro," Eur. J. Cancer 31A:2341 (1995).
Australian First Report on Application No. 2005287375 dated Jun. 10, 2008.
Babiuk, Shawn, Foldvari, Marianna, et al., "Cutaneous vaccination: the skin as an immunologically active tissue and the challenge of antigen delivery," Journal of Controlled Release, vol. 66 Issues 2-3, May 15, 2000 pp. 199-214.
Baker et al., "The Synthesis and Testing of Anti-Cancer Therapeutic Nanodevices," Kluwer Academic Publishers, Manufactured in the Netherlands 61-690 (2001).
Baldwin and Saltzman et al., "Materials for protein delivery in tissue engineering" 1998 Advanced Drug Delivery Reviews vol. 33, pp. 71-86.
Balogh and Tomalia, J. Am. Che. Soc. 120:7355 (1998).

(56) References Cited

OTHER PUBLICATIONS

Balogh et al., "Formation and Characterization of Dendrimer-Based Water Soluble Inorganic Nanocomposities," Proc. of ACS PMSE 77:118 (1997).
Banga et al., "Assessing the potential of skin electroporation for the delivery of protein- and gene-based drugs," Trends in Biotechnology voll. 16 Issue 10, Oct. 1, 1998 pp. 408-412.
Baker et al., "Utilization of Lipophilic Ionic Additives in Liquid Polymer Film Optodes for Selective Anion Activity Measurements," Anal. Chem. 69:990 (1997).
Barth et al., "Boron Neutron Capture Therapy of Brain Tumors: Past History, Current Status, and Future Potential," Cancer Invetigation 14:534 (1996).
Barth, et al., "Boronated Starburst Dendrimer-Monoclonal Antibody Immunoconjugates: Evaluation as a Potential Delivery System for Neutron Capture therapy," Bioconjugate Chem. 5:58 (1994).
Baumann et al., "Simultaneous Visuallization of the Yellow and Green Forms of the Green Fluorescent Protein in Lying Cells," J. Histochem. Cytochem. 46:1073 (1998).
Bell, "Molecular Trees: A New Branch of Chemistry," Science 271:1077-1078 (1996).
Bielinska A. et al., "Regulation of in Vitro Gene Expression Using Antisense Oligonucleotides or . . . " Jun. 1, 1996 Nucleic Acids Research, Oxford University Press, Surrey, GB vol. 24 No. 11.
Bielinska et al. Bioconj Chem 10:843-850 (1999).
Bielinska et al., "Application of membrane-based dendrimer/DNA complexes for solid phase transfection in vitro and in vivo" May 2000 Biomaterials vol. 21, Issue 9, pp. 877-887.
Bielinska et al., "The interaction of plasmid DNA with polyamidoamine dendrimers: . . . " Biochimica et Biophysica Acta 1353:180-190 (1997).
Binkley et al., "FNA ligands to human nerve growth factor," Nuc. Acids Res. 23(16):3198-205 (1995).
Block, Lawrence, "Medicated Applications", Remington's Pharmaceutical Sciences, edited by Gennaro, 1990, 18th Edition, pp. 1596 and 1597.
Botchway, et al., "Novel Visible and Ultraviolet Light Photogeneration of . . . " Photochem., Photobiol. 67(7):635-40 (1998).
Bourassa et al., "Photochemistry of Roussin's Red Salt . . . " JACS 119:2853-60 (1997).
Bourne, et al., "Evaluation of the Effects of Intravascular MR Contrast Media (Gadolinium Dendrimer) on 3D Time of Flight Magnetic Resonance Angiography of the Body,"J. Magn. Reson. Imag., 6:305 (1996).
Brandl et al., "Plastics from Bacteria and for Bacteria: . . . ", Adv. Biochem Eng Biotechnol, 41:77 (1990).
Brasseur et al., "Biological Activities of Phthalocyanines . . . " Photochem., Photobiol., 47:705-11 (1988).
Braunegg et al., "Polyhydroxyalkanoates, biopolyesters from renewable resources: Physiological and engineering aspects,"J. Biotechnol 65(2-3):127 (1998).
Brazeau et al., "In vitro myotoxicity of selected cationic macromolecules used in non-viral gene delivery," Pharm Research 15:680-684 (1998).
Capale et al., "Boronated Epidermal Growth Factor as a Potential Targeting Agent for Boron Neutron Capture Therapy of Brain Tumors," Bioconjugate Chem., 7:7 (1996).
Carel et al., "Structural Requirements for C3d,g/Epstein-Barr Virus Receptor (CR2/CD21) Ligand Binding, Internalization, and Viral Infection," J. Biol. Chem. 265:12293 (1990).
Chan and Nie, "quantum Dot Bioconjugates for Ultrasensitive Nonisotopic Detection," Science 281:2016 (1998).
Chang, et al., "Synthetic Appropaches to Long-Wavelength Absorbing Photosensitizers: Porphyrinone and Derivatives," Proc. SPIE, 1203:281-86 (1990).
Chinese Office Action dated Jan. 16, 2009, CN Patent Application No. 200580034777.9.
Choate et al., "Direct Cutaneous Gene Delivery in Human Genetic Skin Disease," Human Gene Ther 8:1659 (1997).
Choi et al., "Poly(ethylene glycol)-block-poly(L-lysine) Dendrimer: . . . ", Bioconjugate Chem. 10:62-65 (1999).
Cincotta, et al., "Novel Benzophenothiazinium Photosensitizers: Preliminary In-Vivo Results," SPIE Proc. SPIE 1203:202-10 (1990).
Co et al., "Isolation and biochemical characterization of the mammalian reovirus type 3 cell-surface receptor," Proc Natl. Acad. Sci 82:1494 (1985).
Cohen and Tohoku, Exp. Med. 168:351 (1992), Abstract printed on May 1, 2002 (1 page).
Cole et al., "The EBV-Hybridoma Technique and its Application to Human Lung Cancer," in Monoclonal Antibodies and Cancer Therapy, Alan R. Liss, Inc., pp. 77-96 (1985).
Cortese et al., "Identification of biologically active peptides using random libraries displayed on phage," Curr. Opin. Biotechol., 6:73 (1995).
Cote et al., "Generation of human monoclonal antibodies reactive with cellular antigens," Proc. Natl. Acad. Sci. U.S.A. 80:2026-2030 (1983).
Davies, "Synthetic materials for covering burn woulds: Progress towards perfection. Part I. Short term dressing materials," Burns 10:94 (1983).
De Leo and Ford, "Reversible Photolabilzation of NO from Chromium (III)-Coordinated Nitrite. A New Strategy for Nitric Oxide Delivery," JACS 121:1980-81 (1999).
Duncan and Malik, Control Rel. Bioact. Mater. 23:105 (1996).
Duncan and Sat, "Tumour targeting by enhanced permeability and retention (EPR) effect," Ann. Oncol. 9:39 (1998).
Duncan et al., "Polymer Conjugates for Anti-Cancer Agent and DNA Delivery," Polymer Preprints 39:180 (1998).
Dvornic and Tomalia, "Dendritic polymers divergent synthesis: starburst poly(amidoamine) dendrimers," in Salamone (ed.) The Polymeric Materials Encyclopedia: 1996 CRC Press, pp. 1-17.
EP Patent Application No. EP 01 935 316.8, Office Action dated Nov. 30, 2007.
Eppstein et al., "Epidermal growth factor receptor occupancy inhibits vaccinia virus infection," Nature 318:663 (1985).
Sottosanti, "Calcium Sulfate: A Biodegradable and Biocompatible Barrier for Guided Tissue Regeneration," Compendium 13(3):226-8, 230, 232-4 (1992).
Springer et al., " Blood Group Tn-Active Macromolecules from Human . . . " Carbohydr. Res. 178:271-292 (1988).
Stoddart, "Gene Delivery with Dendrimers", Chemical Biology 2006.
Talanian et al., "Substrate Specificities of Caspase Family Proteases," J. Biol. Chem., 272:9677 (1997).
Tang et al., "In Vivo Gene Delivery by Degraded Polyamidoamine Dendrimers," Biocong Chem 7:703 (1996).
Tjandra et al., "Application of mammary serum antigen assay in the management of breast cancer: a preliminary report," Br. J. Surg. 75:811-817 (1988).
Tomalia et al., "Starburst Dendrimers: Molecular-Level Control of Size, Shape, Surface chemistry, Topology, and Flexibility from Atoms to Macroscopic Matter," Chem. Int. Ed. Engl., 29:138-175(1990).
Tomalia et al., "Comb-Burst Dendrimer Topology. New Macromolecular Architecture Derived from Dendritic Grating,"Macromolecule 24:1435-1438 (1999).
Tomalia, "Starburst/Cascade Dendrimers: Fundamental Building Blocks for a New Nanoscopic Chemistry Set," Advanced Materials 6:529 (1994).
Tortora et al., "Synergistic Inhibition of Growth and Induction of Apoptosis by 8-Chloro-cAMP and Paclitaxel or Cisplatin in Human Cancer Cells," Cancer Research 57:5107 (1997).
Trainer, et al., "Gene delivery to the epidermis," Human Mol. Gen 6:1761 (1997).
Tuerk et al., "In vitro evolution of functional nucleic acids: high-affinity FNA ligands of HIV-1 proteins," Gene 137 (1):33-9 (1993).
Uppuluri et al., Tecto(Dendrimer) Core-Shell Molecules: . . . PMSE 80:55 (1999).
Urdea and Horn, "Dendrimer Development," Science 261:534 (1993).

(56) References Cited

OTHER PUBLICATIONS

Van Hest et al., "Polystyrene-Dendrimer Amphiphilic Block Copolymers with a Generation-Dependent Aggregation," Science 268:1592-1595 (1995).
Vasey et al., "Phase I Clinicial and Pharmacokinetic Study of PK1 . . . ", Clin. Cancer Res. 5:83 (1999).
Wagner, "Effects of membrane-active agents in gene delivery," Journal of controlled Release 53:155-158 (1998).
Webber et al., "Characterisation of soluble, salt-loaded, degradable PLGA films and their release of tetracycline," J. Biomed Mater Res 41:18 (1998).
White, et al., "Viral Recptors of the Immunoglobulin Superfamily," Cell 56:725 (1989).
Wiener et al., "Dendrimer-Based Metal Chelates: A New Class of Magnetic Resonance Imaging Contrast Agents," Magn Reson. Med. 31:1 (1994).
Wiener et al., "Targeting Dendrimer-Chelates to Tumors and Tumor Cells Expressing the High-Affinity Folate Receptor," Invest. Radiol. 32:748 (1997).
Wies, et al., "Structure of the influenza virus haemagglutinin complexed with its recptor, sialic acid," Nature 333:426 (1988).
Wilbur et al., "Biotin Reagents for Antibody Pretargeting . . . " Bioconjugate Chem., 9:813 (1998).
Winter, "Formation of the Scab and the Rate of Epithelization of Superficial Wounds in the Skin of the Young Domestic Pig," Nature 193:293 (1962).
Wong et al., "Accuracy and Precision of in Vitro Volumetric Measurements by Three-Dimensional Sonography," Ivest. Rad.31:26 (1996).
Wu et al., "Metal-Chelate-Dendrimer-Antibody Constructs for Use in Radioimmunotherapy and Imaging," Bioorg. Med. Chem. Lett., 4:449 (1994).
Wyrick et al., "Entry of Genital Chlamydia trachomatis into Polarized Human Epithelial Cells," Infect. Imm. 57:2378 (1989).
Ye, et al., "Targeted gene correction: a new strategy for molecular medicine" Mol. Med. Today 4:431 (1998).
Yew et al., "Optimization of Plasmid Vectors for High-Level Expression in Lung Epithelial Cells," Human Gene Ther. 8:575 (1997).
Yin et al., "Architectural Copolymers: Rod-Shaped, Cylindrical Dendrimers," J. Am. Chem. Soc., 120:2678 (1998).
Yu, et al., "Overexpression of ErbB2 blocks Taxol-Induced Apoptosis by Upregulation of p21(cip1), which Inhibits p34 (Cdc2) Kinase," Molecular Cell, 2:581 (1998).
Zaffaroni et al., "Induction of apoptosis by taxol and cisplatin and effect on cell cycle-related proteins in cisplatin-sensitive and resistance human ovarian cancer cells," Brit. J. Cancer 77:1378 (1998).
Zhuo et al. 1999, In vitro release of 5-fluorouracil with cyclic core dendritic polymer, J. of Controlled Release 57:249-257.
Zimmerman et al., "Self-Assembling Dendrimers," Science 271:1095-1098 (1996).
Suzawa, et al., "Synthesis of a Novel Duocarmycin Derivative Du-257 . . . ", Bioorganic & Medicinal Chemistry 8 (2000) 2175-2184.
Yang, Cancer Research, 1997, vol. 53, pp. 4333-4339.
Mojoros et al., Macromolecules, 2003, vol. 36, pp. 5526-5529.
Wu et al., Anti-Cancer Agents in Medicinal Chemistry, Mar. 2006, vol. 6, pp. 167-184.
International Search Report dated Jan. 5, 2010, PCT/US2009/036992, filed Mar. 12, 2009.
Jesse B. Wolinsky and Mark W. Grinstaff, "Therapeutic and diagnostic application of dendrimers for cancer treatment," Advanced Drug Delivery Reviews, Mar. 4, 2008, vol. 60, pp. 1037-1055.
Ulrik Boas and Peter M. H. Heegaard, "Dendrimers in drug research," Chemical Society Review, 2004, vol. 33, pp. 43-63.
Istvan J. Majoros, et al., "Poly(amidoamine) dendrimer-based multifunctional engineered nanodevice for cancer therapy," Journal of Medicinal Chemistry, 2005, vol. 48, pp. 5892-5899.

Tooru Ooya, Jaehwei Lee and Kinam Park, "Hydrotropic dendrimers of generations 4 and 5: Synthesis, characterization and hydrotropic solubilization of paclitaxel," Bioconjugate Chemistry, 2004, vol. 15, pp. 1221-1229.
Anil K. Patri, et al., "Synthesis and in vitro testing of J591 antibody-dendrimer conjugates for targeted prostage cancer therapy," Bioconjugate Chemistry 2004, vol. 15, pp. 1174-1181.
Thomas, Thommey, et al., "Detection and Analysis of Tumor Fluorescence Using a Two-Photon Optical Fiber Probe," Biophysical Journal, vol. 86, Jun. 2004, pp. 3959-3965.
Kolb, et al. (2001) Angewandte Chemie Intl. Ed. 40:2004-2011.
Evans (2007) Australian J. Chem. 60:384-395.
Carlmark, et al. (2009) Chem. Soc. Rev. 38:352-362.
Allen, T.M., Nature Reviews Cancer (2002) 2, (1), pp. 750-763.
Peer, D., et al., Nature Nanotechnology (2007), 2, pp. 751-760.
Esfand et al., "synthesis, Complexation and Pharmaceutical Applications of Tetra-directional Cascade Dendrimers," Pharm Sci., 2:157 (1996).
Farkas et al., "Microscopic and Mesoscopic Spectral Bio-Imaging," SPEI 2678:200 (1997).
Fidler et al., "The Implications of Angiogenesis for the Biology and Therapy of Cancer Metastatis," Cell, 79:185 (1994).
Firey and Rodgers, "Photo-Properties of a Silicon Naphthalocyanine: . . . " Photochem. Photobiol., 45:535-38 (1997).
Folkman et al., "Antiogenesis," Journ. of Biol. Chem. 267(16):10931 (1992).
Folkman et al., "Angiogenic Factors," Science, 235:442 (1987).
Folkman, "Clinical Applications of Research on Angiogenesis," New Eng. J. Med. 333(26):1757 (1995).
Fracasso, et al., "Anti-tumor effects of toxins targeted to the prostate specific membrane antigen," The Prostate, 2002, 53: 9-23.
Frechet, et al., "Self-Condensing Vinyl Polymerization: An Approach to Dendritic Materials," Science 269:1080-1083 (1995).
Frechet, "Functional Polymers and Dendrimers: Reactivity, Molecular Architechture, and Interfacial Energy," Science 263:1710-1715 (1994).
Friedman, "Gene Therapy of Cancer Through Restoration of Tumor-Suppressor Functions?J" Cancer 70:1810 (1992).
Fujiwara et al., "Therapeutic Effect of a Retroviral Wild-Type p53 Expression Vector in an Orthotopic Lung Cancer Model," J. Natl. Cancer Inst., 86:458 (1994).
Gac et al., "Synthesis, Characterisation and in Vivo Behaviour of a Norfloxacin-Poly(L-Lysine Citramide Imide) Conjugate Beraing Mannosyl Residues," J. Drug Target 7(5):393 (2000).
Garcia-Contreras et al., "Biodegradable Cisplatin Microspheres for Direct Brain Injection: Preparation and Characterization," Pharm Dev Tech 2:53 (1997).
Gerwitz et al., "Nucleic Acid Therapeutics: State of the Art and Future Prospects," Blood 92:712 (1998).
Gibb, "Apoptosis as a Measure of Chemosensitivity to Cisplatin and Taxol Therapy in Ovarian Cancer Cell Lines," Gynecologoic Oncology 65:13 (1997).
Goodwin and Meares, Cancer (suppl.) 80:2675 (1997).
Haensler et al., "Polyamidoamine Cascade Polymers Mediate Efficient Transfection of Cells in Culture," Bioconjugate Chem. 4:373-379 (1993).
Hanisch et al., "Structural Studies on Oncofetal Carbohydrate . . . " Carbohydr. Res. 178:29-47 (1988).
Hawker et al., "Unimolecular Micelles and Globular Amphiphiles: Dendritic Macromolecules as Novel Recyclable Solubilization Agents," J. Chem. Soc. Perkins Trans. 12:1287-1297 (1993).
Hinoda et al., "Immunochemical Characterization of Adenocarcinoma-Associated Antigen YH206," Cancer J. 42:653-658 (1988).
Hockenbery et al., "Bcl-2 Functions in an Antioxidant Pathway to Prevent Apoptosis," Cell 75:241 (1993).
Holister et al., "Dendrimers" 2003 Technology White Papers pp. 1-15.
Huse, et al., "Generation of a Large Combinatorial Library of the Immunoglobulin Repertoire in Phage Lambda," Science 246:1275-1281 (1989).
International Search Report mailed Sep. 8, 2008, PCT/US2007/15976.

(56) References Cited

OTHER PUBLICATIONS

International Search Report dated Jul. 8, 2002, PCT/US01/15204.
International Search Report dated Nov. 20, 2001, PCT/US01/40824.
International Search Report mailed Jul. 17, 2006, PCT/US05/30278.
Lester et al., "Infrared Microspectroscopic Imaging of the Cerebellum of Normal and Cytarabine Treated Rats," Cell Mol. Biol. 44:29 (1998).
International Search Report, PCT/Us2008/061023, dated Dec. 16, 2008.
Ishida et al., "Related Glycoproteins from Normal Secretory and Malignant Breast Cells," Tumor Biol. 10:12-22 (1989).
Jain et al., "Controlled Drug Delivery by Biodegradable Poly(Ester) Devices: Different Preparative Approaches," Drug Dev Ind Pharm 24:703 (1998).
Jane et al., "Vector development: a major obstacle in human gene therapy," Annals of Med 30:413 (1998).
Jansen et al., "The Dendritic Box: Shape-Selective Liberation of Encapsulated Guests," J. Am. Chem. Soc. 117:4417-4418 1995.
Jellinek, et al., "Inhibition of Receptor Binding by High-Affinity RNA Ligands to Vascular Endothelial Growth Factor," Biochem 83(34):10450-6 (1994).
Kaner et al., "Fibroblast Growth Factor Receptor is a Portal of Cellular Entry for Herpes Simplex Virus Type 1," Science 248:1410 (1990).
Kannon and Garrett, "Moist Wound Healing with Occlusive Dressings," Ermatol. Surg. 21:583 (1995).
Kerr et al., "Apoptosis: Its Significance in Cancer and Cancer Therapy," Cancer 73:2013 (1994).
Klatzman et al., "T-lymphocyte T4 molecule behaves as the receptor for human retrovirus LAV," Nature 312:767 (1984).
Kirpotin et al., "Sterically Stabilized Anti-HER2 Immunoliposomes: Design and Targeting to Human Breast Cancer Cells in Vitro," Biochem., 36:66 (1997).
Kjeldsen et al., "Preparation and Characterization of Monoclonal Antibodies Directed to the Tumor-associated O-linked . . . " Cancer Res. 48:2214-2220 (1988).
Kohler and Milstein, "Continuous cultures of fused cells secreting antibody of predefined specificity," Nature 256:495-497 (1975).
Kozbor et al. "The production of monoclonal antibodies from human lymphocytes," Immunol. Today 4:72 (1983).
Krah, "Characterization of Octyl Glucoside-Solubilized Cell Membrane Receptors for Binding Measles Virus," Virology 172:386 (1989).
Kuhlmann et al., "Reduction of cisplatin toxicity in cultured renal tubular cells by the bioflavonoid quercetin," Arch. Toxicol. 72:536 (1998).
Kukowska-Latallo et al., "Efficient transfer of genetic material into mammalian cells using Starburst polyamidoamine dendrimers," Proc. Natl. Acad. Sci. USA 93:4897-4902 (1996).
Lan et al., "Isolation and Properties of a Human Pancreatic Adenocarcinoma-associated . . . " Cancer Res. 45:305-310 (1985).
Lanni et al., "p53-independent apoptosis induced by paclitaxel througho an indirect mechanism," Proc. Natl. Acad. Sci., 94:9679 (1997).
Lentz, et al., "Is the Acetylcholine Rectpor a Rabies Virus Receptor," Science 215:182 (1982).
Majithia V, et al. Am. J. Med. (2007) 120 (11): 936-9.
Eichman Et al. (2000) Pharm. Sci. Technolo. Today 3:232-245.
Lou et al. (2002) Macromol. 35:3456-3462.
Kobayashi et al. (2003) Bioconj. Chem. 14:388-394.
Huang, B., et al., "Copper-free click conjugation of methotrexate to a PAMAM dendrimer platform", Tetrahedron Letters, E-pub, Dec. 10, 2010, v. 52, pp. 1411-1414.
Dijk, M.V., et al., "Synthesis and Applications of Biomedical and Pharmaceutical Polymers via Click Chemistry Methodologies," Bioconjugate Chemistry, Nov. 2009, v. 20, No. 11, pp. 2011-2016.
Nimmo, C.M. et al., "Regenerative Biomaterials that 'Click': Simple, Aqueous-Based Protocols for Hydrogel Synthesis, Surface Immoboilization, and 3D Patterning" Bioconjugate Chemistry, Oct. 13, 2011, v. 22, pp. 2199-2209.
Huang, B., et al., "The facile synthesis of multifunctional Pamam dendrimer conjugates through copper-free click chemistry" Bioorganic & Medicinal Chemistry Letters, Mar. 21, 2012, v. 22, pp. 3152-3156.
International Search Report and Written Opinion mailed Mar. 29, 2013, International Patent Application No. PCT/US2012/066104.
Svensson, J.-O, Journal of Chromatography B., Biomedical Sciences and Applications ( )1986) 375, pp. 174-178.
Tebbett, I.R. Chromatographia (187) 23(5), pp. 377-378 , 1987.
Stamford, J.A., Journal of Neuroscience Methods, (1990), 34(1-3), pp. 67-72.
Toner, C.C., and J.A. Stamford, Journal of Neuroscience Methods (1996) 67(2), pp. 133-140.
Toner, C.D. and J.A. Stamford, Neuroscience (1997), 81(4), pp. 999-1007.
Kimiskidis, V., et al., 2007, "Development and validation of a high performance liquid chromatographic method for the determination of oxcarbazepine and its main metabolites in human plasma and cerebrospinal fluid and its application to pharmacokinetic study", J Pharm Biomed Anal.; 43(2):763-8.
Achilli, G., et al., Journal of Chromatography, A. (1996) 729(1-2), pp. 273-277.
Horner, K.A., et al., Brain Research (2004) 1028(2): pp. 121-132.
Childers, S.R. and S.R. Childers, Life Sciences (1991) 48(21): pp. 1991-2003.
Adams, J.D., Jr., et al. Biomedical Mass Spectometry (1981) 8(11): pp. 527-538.
Millhorn et al, 1996, "Regulation of ionic conductances and gene expression by hypoxia in an oxygen sensitive cell line.", Adv Exp Med Biol. 410:135-42.
Cai, Y.C., et al., "Molecular Pharmacology," (1997) 51(4), pp. 583-587.
Franklin, R,B., et al., BMC Biochemistry (2006) 7: p. 10.
Kukanich, B., et al., Therapeutic Drug Monitoring (2005) 27(3), pp. 389-392.
Cucullo, L., et al., Current Opinion in Drug Discovery & Development (2005) 8(1), pp. 88-99.
Nambiar, M.P., et al., Toxicology and Applied Pharmacology (2007) 219(2-3), pp. 142-150.
Shih, T.M., T.C. Rowland and J.H. McDonough, Journal of Pharmacology and Experimental Therapeutics (2007) 320 (1), pp. 154-161.
Schulte, H., A. Sollevi and M. Segeradahl, Pain, (2005) 116(3), pp. 366-374.
Loetsch, J., et al., Clinical Pharmacology and Therapeutics (1996) 60(3): pp. 316-325.
Hill, H.F., et al., Pain (1990) 43(1), pp. 57-79.
Worek, F., et al., Toxicology (2008). 244: pp. 35-41.
CN Office Action mailed Aug. 14, 2013, CN Patent Application No. 201080059383.
Bhanja, et al., "Protective role of R-spondin1, an intestinal stem cell growth factor, against radiation-induced gastrointestinal syndrome in mice," Plos One, vol. 4, Issue 11, Article No. e8014, pp. 1-10 (Nov. 24, 2009).
Zhao, et al., "R-spondin1 protects mice from chemotheray or radiation-induced oral mucositis through the canonical Wnt/B-catein pathway," PNAS, vol. 106, No. 7, pp. 2331-2336 (Feb. 17, 2009).
Zhou, et al., "Slit-Robo signaling induces malignant transormation through Hakai-mediated E-cadher in degration during colorectal epithelial cell carcinogenesis", Cell Research, vol. 21, No. 4, pp. 609-626 (Feb. 1, 2011).
Wang, eet al., "Induction of tumor angiogenesis by Slit-Robo signaling and inhibition of cancer growth by blocking Robo activity," Cancer Cell, vol. 4, Issue 1, pp. 19-29 (Jul. 2003).
Takashima et al., "The Wnt agonist R-spondin1 regulates systemic graft-versus-host disease by protecting intestinal stem cells," The Journal of Experimental Medicine, vol. 208, No. 2, pp. 285-294 (Jan. 31, 2011).
Zhou, et al., "Induction of intestinal stem cells by R-spondin1 and slit2 augments chemoradioprotection," Nature, vol. 501, No. 7465, pp. 107-111 (Sep. 2013).

* cited by examiner

MULTIFUNCTIONAL SMALL MOLECULES

CROSS-REFERENCE TO RELATED APPLICATION

This application is a U.S. 371 national phase entry of International Patent Application No. PCT/US2010/050893, international filing date Sep. 30, 2010 which claims priority to U.S. Provisional Patent Application No. 61/256,699, filed Oct. 30, 2009, the contents of which are herein incorporated by reference in their entireties.

STATEMENT REGARDING FEDERALLY SPONSORED RESEARCH OR DEVELOPMENT

This invention was made with government support under contract number R01 CA119409 awarded by the National Institutes of Health. The government has certain rights in the invention.

FIELD OF THE INVENTION

The present invention relates to dendrimer synthesis. Specifically, the present invention relates to triazine compositions (e.g., scaffolds) capable of click chemistry for use in one-step synthesis of functionalized dendrimers, and methods of use of the same.

BACKGROUND OF THE INVENTION

Cancer remains the number two cause of mortality in the United States, resulting in over 500,000 deaths per year. Despite advances in detection and treatment, cancer mortality remains high. New compositions and methods for the imaging and treatment (e.g., therapeutic) of cancer may help to reduce the rate of mortality associated with cancer.

Severe, chronic pain is observed on a variety of subjects. For example, there exist large numbers of individuals with severe pain associated with arthritis, autoimmune disease, injury, cancer, and a host of other conditions.

There exists a need for compositions, methods and systems for delivering agents (e.g., diagnostic and/or therapeutic (e.g., cancer therapeutics, pain relief agents) to subjects that provide effective therapy (e.g., disease treatment, symptom relief, etc.) with reduced or eliminated side effects, even when administered in high doses. Functionalized dendrimers, such as PAMAM dendrimers conjugated with functional ligands relevant to cancer therapy and/or pain alleviation, have been developed for such purposes. However, multi-step conjugation strategies used to attach different functional groups to the surfaces of nanoparticles (e.g., dendrimers, PAMAM dendrimer branches) introduce higher polydispersity and require multiple processing steps, thereby complicating synthesis. In addition, increased polydispersity of functionalized dendrimer products can negatively affect properties such as therapeutic potency, pharmacokinetics, or effectiveness for multivalent targeting.

Improved methods of synthesis of dendrimers resulting in decreased polydispersity are needed. In particular, compositions and methods that facilitate one-step "click" chemistry for use in synthesis of functionalized dendrimers are needed.

SUMMARY OF THE INVENTION

The present invention relates to dendrimer synthesis. Specifically, the present invention relates to triazine compositions (e.g., scaffolds) capable of click chemistry for use in one-step synthesis of functionalized dendrimers and methods of synthesizing and using the same.

Functionalized dendrimers, such as PAMAM dendrimers conjugated with functional ligands (e.g., therapeutic agents, triggering agents, imaging agents, targeting agents) have many therapeutic and diagnostic applications. However, multi-step conjugation strategies used to attach different functional ligands to the surfaces of nanoparticles (e.g., dendrimers, PAMAM dendrimer branches) introduce higher polydispersity and require multiple processing steps, thereby complicating synthesis and negatively affecting properties such as therapeutic potency, pharmacokinetics, or effectiveness for multivalent targeting.

For example, multifunctional cancer therapeutics have been developed based on Generation 5 PAMAM dendrimers (G5) (see, e.g., Majoros, I. J.; et al., J Med Chem 2005, 48, 5892; Thomas, T. P.; et al., J Med Chem 2005, 48, 3729; Kukowska-Latallo, J. F.; et al., Cancer Res 2005, 65, 5317; Zhang, Y. H.; et al., Bioconjugate Chem 2010, 21, 489; each herein incorporated by reference in their entireties). The targeting molecule folic acid (FA) and the chemotherapeutic drug methotrexate (MTX) were conjugated sequentially through amide- and ester-linkages, respectively (see, e.g., Majoros, I. J.; et al., J Med Chem 2005, 48, 5892; herein incorporated by reference in its entirety). Although this device was shown to bind and selectively kill KB tumor cells that over-express folate receptor (FR) in vitro and in vivo (see, e.g., Thomas, T. P.; et al., J Med Chem 2005, 48, 3729; Kukowska-Latallo, J. F.; et al., Cancer Res 2005, 65, 5317; each herein incorporated by reference in its entireties), the multi-step conjugation strategy that was employed resulted in a mixture of dendrimer populations having varying distributions of the targeting ligands (FA and MTX). The resulting polydispersity was more severe and problematic during large-scale synthesis of the conjugate, which hindered attempts to move into clinical trials. This was because, for example, the polydisperisty of the functionalized dendrimer-based therapeutics likely negatively affected properties such as therapeutic potency, pharmacokinetics, and effectiveness for multivalent targeting (see, e.g., Gillies, E. R.; et al., Drug Discov Today 2005, 10, 35; herein incorporated by reference its entirety). Moreover, multi-step conjugations make batch-to-batch reproducibility extremely challenging, as the characterization required after each step becomes progressively more difficult (see, e.g., Mullen, D. G.; et al., Bioconjugate Chem 2008, 19, 1748; Mullen, D. G.; Acs Nano 2010, 4, 657; each herein incorporated by reference in their entireties). The present invention overcomes such issues and provides improved methods for the synthesis of well-defined multifunctional dendrimers.

It has been previously shown that modifications to the side chains of the glutamic acid moiety on both FA and MTX can be made without loss of activity (see, e.g., Rosowsky, A.; et al., J Med Chem 1981, 24, 1450; Wang, S.; et al., Bioconjugate Chem 1996, 7, 56; each incorporated by reference in their entireties). The simplest approach for coupling FA or MTX to a PAMAM dendrimer is through non-selective activation of the carboxyl groups of the glutamic acid moiety by carbodiimide (see, e.g., Majoros, I. J.; et al., J Med Chem 2005, 48, 5892; herein incorporated by reference in its entirety). Unfortunately, this method leads to the formation of two structural isomers in which FA and MTX are linked through either the α- or γ-carboxyl group. It has been reported that FA linked via γ-carboxyl group retains a stronger affinity toward its receptor (see, e.g., Wang, S.; et al., Bioconjugate Chem 1996, 7, 56; herein incorporated by reference in its entirety). It also has been shown that a free α-carboxyl group is essential for retaining MTX's binding to target enzymes such as dihydrofolate reductase (DHFR), whereas chemical modifications of the γ-carboxyl group are much better tolerated (see, e.g., Wells, X. E.; et al., Drug Develop Res 1999, 46, 302; herein incorporated by reference in its entirety). In addition, the availability of multiple amino functional groups on the dendrimer surface allows for the nonspecific reaction with the α- and γ-carboxyl groups of MTX and FA, leading to the formation of inactive conjugates where both carboxyl groups have been coupled. Furthermore, dendrimer dimers can form with MTX and/or FA serving as a covalent bridge. Therefore, precise control of these coupling reactions is necessary to preserve the therapeutic activity of the conjugate.

The present invention utilizes, for example, triazine scaffolds (e.g., trivalent reagent 2,4,6-trichloro-1,3,5-triazines as a core scaffold) to give access to multifunctional architectures, thereby enabling replacing several chemical entities with a single molecule. Indeed, experiments conducted during the course of developing some embodiments of the present invention determined that multivalent triazine compounds (e.g., triazine scaffolds) find use in one-step (e.g., click chemistry) synthesis of functionalized dendrimers. Moreover, experiments conducted during the course of developing some embodiments of the present invention demonstrated that such derivatives (e.g., triazine derivatives incorporating the targeting moiety FA and therapeutic drug MTX conjugated to PAMAM dendrimers through "click chemistry") demonstrated an in vitro dose-dependent cytotoxicity with higher cytotoxic potential vs. a similar conjugate synthesized by a multi-step approach (see, e.g., FIGS. 9 and 10 and Example III).

The present invention is not limited to particular triazine compounds (e.g., triazine scaffolds). In some embodiments, the triazine scaffolds comprise a ring structure (e.g., comprising three nitrogen atoms). The triazine scaffolds are not limited to a particular type or kind of triazine ring structure. In some embodiments, the ring structure is six-membered (e.g., the molecular formula comprises $C_3H_3N_3$). In some embodiments, the ring is a conjugated system. For example, triazine moieties with six-membered rings may have nitrogen atoms at any possible placement so long as three nitrogen atoms occur in the ring (e.g., 1,2,3-triazine; 1,2,4-triazine, 1,3,5-triazine, 1,2,5-triazine, 1,2,6-triazine, etc.). Examples of triazine scaffolds include, but are not limited to,

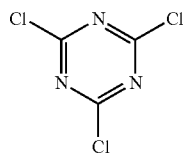

(e.g., 2,4,6-trichloro-1,3,5-triazine),

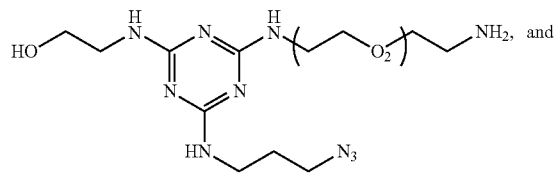 and

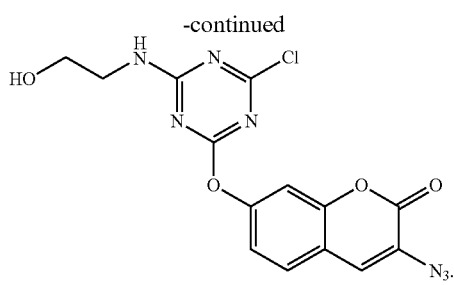

The triazine scaffolds are not limited to a particular manner of synthesis. In some embodiments, the triazine scaffolds are synthesized from cyanuric chloride by consecutive aromatic nucleophilic substitution reactions (e.g., as described in Example 2).

In experiments conducted during the development of embodiments for the present invention, trivalent triazine small molecules were used as a core scaffold on which two sites were used for binding (e.g., conjugation) to functional ligands and a third site was used for conjugation to an azide linker. It was determined that the linker itself can be functionalized (e.g., 3-azido-coumarine finds use as an imaging agent). The elaborated triazine scaffold was then used for one-step "click chemistry" reaction with an alkyne-modified PAMAM dendrimer, resulting in a functionalized dendrimer (e.g., nanodevice). It was determined that the azide-containing linker (e.g., 3-azido-coumarine) is fluorescence-silent prior to the click chemistry reaction, and fluoresces after conjugation to the alkyne-modified PAMAM dendrimer, thereby providing a means to monitor dendrimer modification. Moreover, one-step reaction of dendrimer (e.g., modified dendrimers, modified dendrimer terminal branches) with a multivalent triazine scaffold resulted in decreased polydispersity of the final functionalized nanodevice product.

The present invention is not limited to utilizing a particular type or form of dendrimer. Indeed, examples of dendrimers finding use in the present invention include, but are not limited to, PAMAM dendrimer, a Baker-Huang PAMAM dendrimer (see, e.g., U.S. Provisional Patent Application No. 61/251,244, herein incorporated by reference in its entirety), a polypropylamine (POPAM) dendrimer, and a PAMAM-POPAM dendrimer. The type of dendrimer used is not limited by the generation number of the dendrimer. Dendrimer molecules may be generation 0, generation 1, generation 2, generation 3, generation 4, generation 5, generation 6, generation 7, or higher than generation 7. In some embodiments, half-generation dendrimers may be used. In certain embodiments, a generation 5 amine-terminated PAMAM dendrimer is used. In certain embodiments, a generation 5 alkyne-terminated PAMAM dendrimer is used. In some embodiments, the dendrimer is at least partially acetylated.

Dendrimers are not limited by their method of synthesis. The dendrimer may be synthesized by divergent synthesis methods or convergent synthesis methods. In certain embodiments of the present invention, dendrimer molecules may be modified. Modifications may include but are not limited to the addition of amine-blocking groups (e.g., acetyl groups), ligands, functional groups, conjugates, and/or linkers not originally present on the dendrimer. Modification may be partial or complete. In some embodiments, all of the termini of the dendrimer molecules are modified. In some embodiments, not all of the dendrimer molecules are modified. In preferred embodiments, methods and systems of the present invention permit identification and isolation of subpopulations of dendrimers with known numbers of ligand attachments (e.g., conjugations) per dendrimer molecule, thereby yielding samples or subpopulations of dendrimer compositions with high structural uniformity.

The present invention is not limited to particular ligand types (e.g., functional groups) (e.g., for conjugation with dendrimers and/or with triazine scaffolds). Examples of ligand types (e.g., functional groups) include but are not limited to therapeutic agents, targeting agents, trigger agents, and imaging agents. In some embodiments, the ligand is an alkyne ligand that includes an alkyne group. In some embodiments, the ligand is an azide ligand that includes an azido group. In some embodiments, the ligand includes an aromatic group. Methods, systems, and compositions of the present invention are not limited by the number of different ligand types used. There may be 1, 2, 3, 4, 5, 6, 7, 8, 9, 10 or more different types of ligands attached to a dendrimer molecule.

In some embodiments, conjugation between a ligand and a functional group or between functional groups is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (or equivalent thereof) (or any active end group such as, for example, a primary amine end group, a hydroxyl end group, a carboxylic acid end group, a thiol end group, etc.) on the second moiety. 'Click chemistry' is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

The present invention is not limited to particular functional groups (e.g., for conjugation with dendrimers). Examples of functional groups include but are not limited to therapeutic agents, targeting agents, trigger agents, and imaging agents.

In some embodiments, the functional group(s) is attached with the dendrimer via a linker. The present invention is not limited to a particular type or kind of linker. In some embodiments, the linker comprises a spacer comprising between 1 and 8 straight or branched carbon chains. In some embodiments, the straight or branched carbon chains are unsubstituted. In some embodiments, the straight or branched carbon chains are substituted with alkyls.

Examples of therapeutic agents include, but are not limited to, a chemotherapeutic agent, an anti-oncogenic agent, an anti-angiogenic agent, a tumor suppressor agent, an anti-microbial agent, an expression construct comprising a nucleic acid encoding a therapeutic protein, a pain relief agent, a pain relief agent antagonist, an agent designed to treat an inflammatory disorder, an agent designed to treat an autoimmune disorder, an agent designed to treat inflammatory bowel disease, and an agent designed to treat inflammatory pelvic disease. In some embodiments, the agent designed to treat an inflammatory disorder includes, but is not limited to, an anti-rheumatic drug, a biologicals agent, a nonsteroidal anti-inflammatory drug, an analgesic, an immunomodulator, a glucocorticoid, a TNF-α inhibitor, an IL-1 inhibitor, and a metalloprotease inhibitor. In some embodiments, the anti-rheumatic drug includes, but is not limited to, leflunomide, methotrexate, sulfasalazine, and hydroxychloroquine. Examples of biologicals agents include, but are not limited to, rituximab, finfliximab, etanercept, adalimumab, and golimumab. In some embodiments, the nonsteroidal anti-inflammatory drug includes, but is not limited to, ibuprofen, celecoxib, ketoprofen, naproxen, piroxicam, and diclofenac. In some embodiments, the analgesic includes, but is not limited to, acetaminophen, and tramadol. In some embodiments, the immunomodulator includes but is not limited to anakinra, and abatacept. In some embodiments, the glucocorticoid includes, but is not limited to, prednisone, and methylprednisone. In some embodiments, the TNF-α inhibitor includes but is not limited to adalimumab, certolizumab pegol, etanercept, golimumab, and infliximab. In some embodiments, the autoimmune disorder and/or inflammatory disorder includes, but is not limited to, arthritis, psoriasis, lupus erythematosus, Crohn's disease, and sarcoidosis. In some embodiments, examples of arthritis include, but are not limited to, osteoarthritis, rheumatoid arthritis, septic arthritis, gout and pseudo-gout, juvenile idiopathic arthritis, psoriatic arthritis, Still's disease, and ankylosing spondylitis.

Ligands suitable for use in certain method embodiments of the present invention are not limited to a particular type or kind of targeting agent. In some embodiments, the targeting agent is configured to target the composition to cancer cells. In some embodiments, the targeting agent comprises FA. In some embodiments, the targeting agent binds a receptor selected from the group consisting of CFTR, EGFR, estrogen receptor, FGR2, folate receptor, IL-2 receptor, and VEGFR. In some embodiments, the targeting agent comprises an antibody that binds to a polypeptide selected from the group consisting of p53, Muc1, a mutated version of p53 that is present in breast cancer, HER-2, T and Tn haptens in glycoproteins of human breast carcinoma, and MSA breast carcinoma glycoprotein. In some embodiments, the targeting agent comprises an antibody selected from the group consisting of human carcinoma antigen, TP1 and TP3 antigens from osteocarcinoma cells, Thomsen-Friedenreich (TF) antigen from adenocarcinoma cells, KC-4 antigen from human prostrate adenocarcinoma, human colorectal cancer antigen, CA125 antigen from cystadenocarcinoma, DF3 antigen from human breast carcinoma, and p97 antigen of human melanoma, carcinoma or orosomucoid-related antigen. In some embodiments, the targeting agent is configured to permit the composition to cross the blood brain barrier. In some embodiments, the targeting agent is transferrin. In some embodiments, the targeting agent is configured to permit the composition to bind with a neuron within the central nervous system. In some embodiments, the targeting agent is a synthetic tetanus toxin fragment. In some embodiments, the synthetic tetanus toxin fragment comprises an amino acid peptide fragment. In some embodiments, the amino acid peptide fragment is HLNILSTLWKYR (SEQ ID NO: 2).

In some embodiments, the ligand comprises a trigger agent. The present invention is not limited to particular type or kind of trigger agent. In some embodiments, the trigger agent is configured to have a function such as, for example, a) a delayed release of a functional group from the dendrimer, b) a constitutive release of the therapeutic agent from the dendrimer, c) a release of a functional group from the dendrimer under conditions of acidosis, d) a release of a functional group from a dendrimer under conditions of hypoxia, and e) a release of the therapeutic agent from a dendrimer in the presence of a brain enzyme. Examples of trigger agents include, but are not limited to, an ester bond, an amide bond, an ether bond, an indoquinone, a nitroheterocyle, and a nitroimidazole.

Ligands suitable for use in certain method embodiments of the present invention are not limited to a particular type or kind of imaging agent. Examples of imaging agents include, but are not limited to, fluorescein isothiocyanate (FITC), 6-TAMARA, acridine orange, and cis-parinaric acid.

In certain embodiments, the present invention provides a composition comprising a PAMAM dendrimer conjugated with a triazine compound. In some embodiments, the PAMAM dendrimer is conjugated with the triazine compound via a 3-azido-coumarine linkage agent. In some embodiments, the triazine compound comprises a 1,3,5-triazine compound. In some embodiments, the triazine compound is trivalent. In some embodiments, the triazine compound is conjugated with one or more ligands. In some embodiments, the one or more ligands are independently selected from types such as a therapeutic agent, a targeting agent, an imaging agent, and a trigger agent. In some embodiments, the one or more ligands are MTX, FA, and 3-azido-coumarine. In some embodiments, the triazine compound is configured to be compatible with click chemistry. In some embodiments, the triazine compound comprises an azido group. In some embodiments, the triazine compound is a compound such as

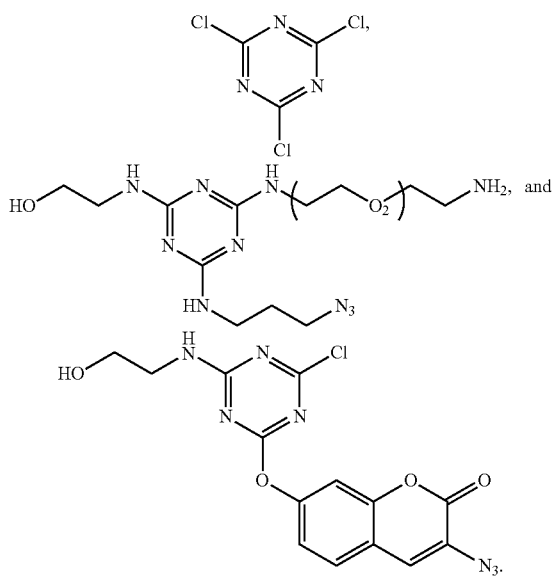

In certain embodiments, the present invention provides a method of synthesizing a functionalized dendrimer, the method comprising: a) providing an alkyne-modified dendrimer (e.g., PAMAM dendrimer) and a triazine compound; and b) conjugating the alkyne-modified dendrimer with the triazine compound. In some embodiments, the conjugating of the alkyne-modified dendrimer (e.g., PAMAM dendrimer) with the triazine compound occurs via a click chemistry reaction. In some embodiments, the dendrimer (e.g., Baker-Huang PAMAM dendrimer; PAMAM dendrimer) is conjugated with the triazine compound via a 3-azido-coumarine linkage agent. In some embodiments, the method further comprises: step c) conjugating one or more ligands with the triazine compound. In some embodiments, the one or more ligands are types such as a therapeutic agent, a targeting agent, an imaging agent, and a trigger agent. In some embodiments, the one or more ligands are MTX and FA. In some embodiments, the triazine compound comprises an azido group.

In certain embodiments, the present invention provides methods for treating a disorder selected from the group consisting of any type of cancer or cancer-related disorder (e.g., tumor, a neoplasm, a lymphoma, or a leukemia), a neoplastic disease, osteoarthritis, rheumatoid arthritis, septic arthritis, gout and pseudo-gout, juvenile idiopathic arthritis, psoriatic arthritis, Still's disease, and ankylosing spondylitis, comprising administering to a subject suffering from the disorder a dendrimer generated with the methods of the present invention. In some embodiments, the dendrimer is co-administered with an additional agent(s) so as to enhance such a treatment.

Additional embodiments will be apparent to persons skilled in the relevant art based on the teachings contained herein.

DEFINITIONS

Figure 1:
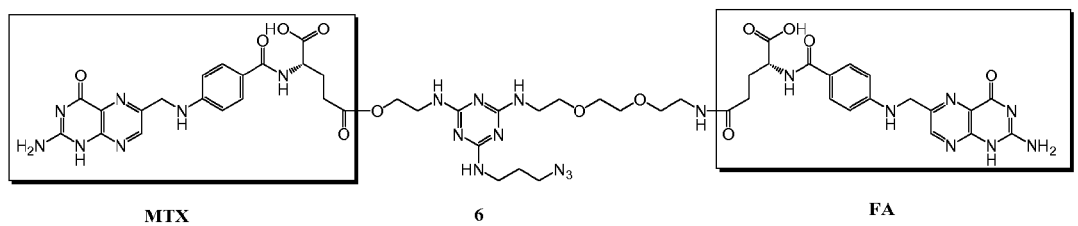
FIG. 1 shows molecular structures of triazines 6 and 9.
Figure 1:
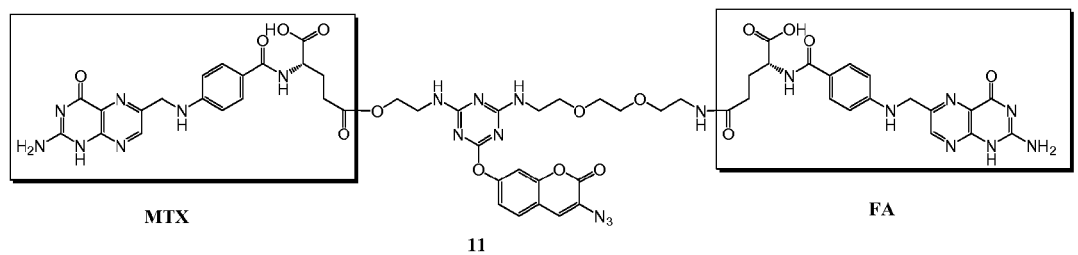

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to a test result of initial cancer diagnosis that reveals the presence or absence of cancerous cells (e.g., using a biopsy and histology).

As used herein, the term "identifying the risk of said tumor metastasizing" refers to the relative risk (e.g., the percent chance or a relative score) of a tumor metastasizing.

As used herein, the term "identifying the risk of said tumor recurring" refers to the relative risk (e.g., the percent chance or a relative score) of a tumor recurring in the same organ as the original tumor.

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer on a subject's future health (e.g., expected morbidity or mortality, the likelihood of getting cancer, and the risk of metastasis).

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "purified" or "to purify" or "compositional purity" refers to the removal of components (e.g., contaminants) from a sample or the level of components (e.g., contaminants) within a sample. For example, unreacted moieties, degradation products, excess reactants, or byproducts are removed from a sample following a synthesis reaction or preparative method.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using screening methods known in the art.

As used herein, the term "nanodevice" or "nanodevices" refer, generally, to compositions comprising dendrimers of the present invention. As such, a nanodevice may refer to a composition comprising a dendrimer of the present invention that may contain one or more ligands, linkers, and/or functional groups (e.g., a therapeutic agent, a targeting agent, a trigger agent, an imaging agent) conjugated to the dendrimer.

As used herein, the term "degradable linkage," when used in reference to a polymer refers to a conjugate that comprises a physiologically cleavable linkage (e.g., a linkage that can be hydrolyzed (e.g., in vivo) or otherwise reversed (e.g., via enzymatic cleavage). Such physiologically cleavable linkages include, but are not limited to, ester, carbonate ester, carbamate, sulfate, phosphate, acyloxyalkyl ether, acetal, and ketal linkages (See, e.g., U.S. Pat. No. 6,838,076, herein incorporated by reference in its entirety). Similarly, the conjugate may comprise a cleavable linkage present in the linkage between the dendrimer and functional group, or, may comprise a cleavable linkage present in the polymer itself (See, e.g., U.S. Pat. App. Nos. 20050158273 and 20050181449, each of which is herein incorporated by reference in its entirety).

A "physiologically cleavable" or "hydrolysable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond (e.g., typically a covalent bond) that is substantially stable in water (i.e., does not undergo hydrolysis under physiological conditions to any appreciable extent over an extended period of time). Examples of hydrolytically stable linkages include, but are not limited to, carbon-carbon bonds (e.g., in aliphatic chains), ethers, amides, urethanes, and the like.

As used herein, the term "NAALADase inhibitor" refers to any one of a multitude of inhibitors for the neuropeptidase NAALADase (N-acetylated-alpha linked acidic dipeptidase). Such inhibitors of NAALADase have been well characterized. For example, an inhibitor can be selected from the group comprising, but not limited to, those found in U.S. Pat. No. 6,011,021, herein incorporated by reference in its entirety.

As used herein, the term "Baker-Huang dendrimer" or "Baker-Huang PAMAM dendrimer" refers to a dendrimer comprised of branching units of structure:

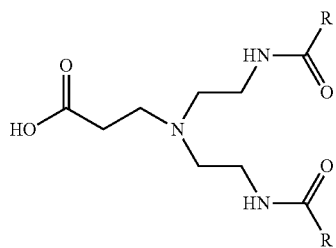

wherein R comprises a carbon-containing functional group (e.g., $CF_3$). In some embodiments, the branching unit is activated to its HNS ester. In some embodiments, such activation is achieved using TSTU. In some embodiments, EDA is added. In some embodiments, the dendrimer is further treated to replace, e.g., $CF_3$ functional groups with $NH_2$ functional groups; for example, in some embodiments, a $CF_3$-containing version of the dendrimer is treated with $K_2CO_3$ to yield a dendrimer with terminal $NH_2$ groups (for example, as shown in Scheme 2). In some embodiments, terminal groups of a Baker-Huang dendrimer are further derivatized and/or further conjugated with other moieties. For example, one or more functional ligands (e.g., for therapeutic, targeting, imaging, or drug delivery function(s)) may be conjugated to a Baker-Huang dendrimer, either via direct conjugation to terminal branches or indirectly (e.g., through linkers, through other functional groups (e.g., through an OH— functional group)). In some embodiments, the order of iterative repeats from core to surface is amide bonds first, followed by tertiary amines, with ethylene groups intervening between the amide bond and tertiary amines. In preferred embodiments, a Baker-Huang dendrimer is synthesized by convergent synthesis methods.

As used herein, the term "click chemistry" refers to chemistry tailored to generate substances quickly and reliably by joining small modular units together (see, e.g., Kolb et al. (2001) Angewandte Chemie Intl. Ed. 40:2004-2011; Evans (2007) Australian J. Chem. 60:384-395; Carlmark et al. (2009) Chem. Soc. Rev. 38:352-362; each herein incorporated by reference in its entirety).

As used herein, the term "triazine" refers to a compound comprising a ring structure bearing three nitrogen atoms. In some embodiments, the ring structure is six-membered (e.g., the molecular formula comprises $C_3H_3N_3$). In some embodiments, the ring is a conjugated system. Triazine moieties with six-membered rings may have nitrogen atoms at any possible placement so long as three nitrogen atoms occur in the ring (e.g., 1,2,3-triazine; 1,2,4-triazine, 1,3,5-triazine, 1,2,5-triazine, 1,2,6-triazine, etc.)

As used herein, the term "scaffold" refers to a compound to which other moieties are attached (e.g., conjugated). In some embodiments, a scaffold is conjugated to bioactive functional conjugates (e.g., a therapeutic agent, a targeting agent, a trigger agent, an imaging agent). In some embodiments, a scaffold is conjugated to a dendrimer (e.g., a PAMAM dendrimer). In some embodiments, conjugation of a scaffold to a dendrimer and/or a functional conjugate(s) is direct, while in other embodiments conjugation of a scaffold to a dendrimer and/or a functional conjugate(s) is indirect, e.g., an intervening linker is present between the scaffold compound and the dendrimer, and/or the scaffold and the functional conjugate(s).

As used herein, the term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants. In some embodiments, conjugation between a dendrimer (e.g., a terminal arm of a dendrimer) and a functional ligand is accomplished during a "one-pot" reaction. In some embodiments, a one-pot reaction occurs wherein a hydroxyl-terminated dendrimer (e.g., HO-PAMAM dendrimer) is reacted with one or more functional ligands (e.g., a therapeutic agent, a pro-drug, a trigger agent, a targeting agent, an imaging agent) in one vessel, such conjugation being facilitated by ester coupling agents (e.g., 2-chloro-1-methylpyridinium iodide and 4-(dimethylamino) pyridine) (see, e.g., International Patent Application No. PCT/US2010/042556, herein incorporated by reference in its entirety).

As used herein, the term "solvent" refers to a medium in which a reaction is conducted. Solvents may be liquid but are not limited to liquid form. Solvent categories include but are not limited to nonpolar, polar, protic, and aprotic.

As used herein, the term "dialysis" refers to a purification method in which the solution surrounding a substance is exchanged over time with another solution. Dialysis is generally performed in liquid phase by placing a sample in a chamber, tubing, or other device with a selectively permeable membrane. In some embodiments, the selectively permeable membrane is cellulose membrane. In some embodiments, dialysis is performed for the purpose of buffer exchange. In some embodiments, dialysis may achieve concentration of the original sample volume. In some embodiments, dialysis may achieve dilution of the original sample volume.

As used herein, the term "precipitation" refers to purification of a substance by causing it to take solid form, usually within a liquid context. Precipitation may then allow collection of the purified substance by physical handling, e.g. centrifugation or filtration.

As used herein, an "ester coupling agent" refers to a reagent that can facilitate the formation of an ester bond between two reactants. The present invention is not limited to any particular coupling agent or agents. Examples of coupling agents include but are not limited to 2-chloro-1-methylpyridium iodide and 4-(dimethylamino) pyridine, or dicyclohexylcarbodiimide and 4-(dimethylamino) pyridine or diethyl azodicarboxylate and triphenylphosphine or other carbodiimide coupling agent and 4-(dimethylamino)pyridine.

As used herein, the term "glycidolate" refers to the addition of a 2,3-dihydroxylpropyl group to a reagent using glycidol as a reactant. In some embodiments, the reagent to which the 2,3-dihydroxylpropyl groups are added is a dendrimer. In some embodiments, the dendrimer is a PAMAM dendrimer. Glycidolation may be used generally to add terminal hydroxyl functional groups to a reagent.

As used herein, the term "ligand" refers to any moiety covalently attached (e.g., conjugated) to a dendrimer branch; in preferred embodiments, such conjugation is indirect (e.g., an intervening moiety exists between the dendrimer branch and the ligand) rather than direct (e.g., no intervening moiety exists between the dendrimer branch and the ligand). Indirect attachment of a ligand to a dendrimer may exist where a scaffold compound (e.g., triazine scaffold) intervenes. In preferred embodiments, ligands have functional utility for specific applications, e.g., for therapeutic, targeting, imaging, or drug delivery function(s). The terms "ligand", "conjugate", and "functional group" may be used interchangeably.

DETAILED DESCRIPTION OF THE INVENTION

Polymers have been used as drug carriers due to their ability to release drugs in a controlled manner, prolong circulation times, and increase drug solubility. Major efforts have been made to synthesize functional polymers that lead to the components of multipurpose therapeutic or diagnostic materials. Because of their well-defined structures with precise control of the size and shape as well as terminal functional groups, PAMAM dendrimers are well suited to serve as a platform for the development of an effective tumor targeting drug delivery device (Tekade et al. (2009) Chem. Rev. 109: 49-87; Landers et al. (2002) J. Infect. Dis. 186:1222-1230; Weiner et al. (1997) Invest. Radiol. 32:748-754; Delong et al. (1997) J. Pharm. Sci. 86:762-764; Gillies et al. (2005) Drug Discovery Today 10:35-43; each herein incorporated by reference in its entirety). A multi-step synthetic procedure is commonly employed to synthesize the multifunctional dendrimers (Kukowska-Latallo et al. (2005) Canc. Res. 65:5317-5324; Thomas et al. (2005) J. Med. Chem. 48:3729-3735; Quintana et al. (2002) Pharmaceu. Res. 19:1310-1316; each herein incorporated by reference in its entirety). However, multi-step procedures introduce higher polydispersity, which has limited their application. Moreover, it is extremely difficult to precisely characterize the attached components after each procedure. In some embodiments, methods of the present invention provide conjugation of dendrimers with multifunctional small molecule architectures, which are loaded with different bioactive molecules. These small molecule derivatives can be easily purified and characterized before attachment to the dendrimers.

Figure 2:
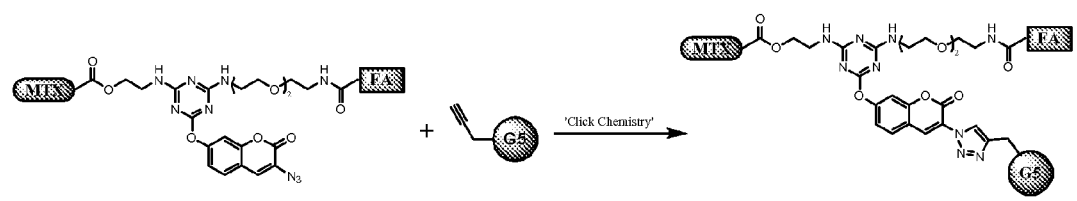
FIG. 2 shows one-step surface modification of the G5 PAMAM dendrimer by click chemistry.
Figure 3:
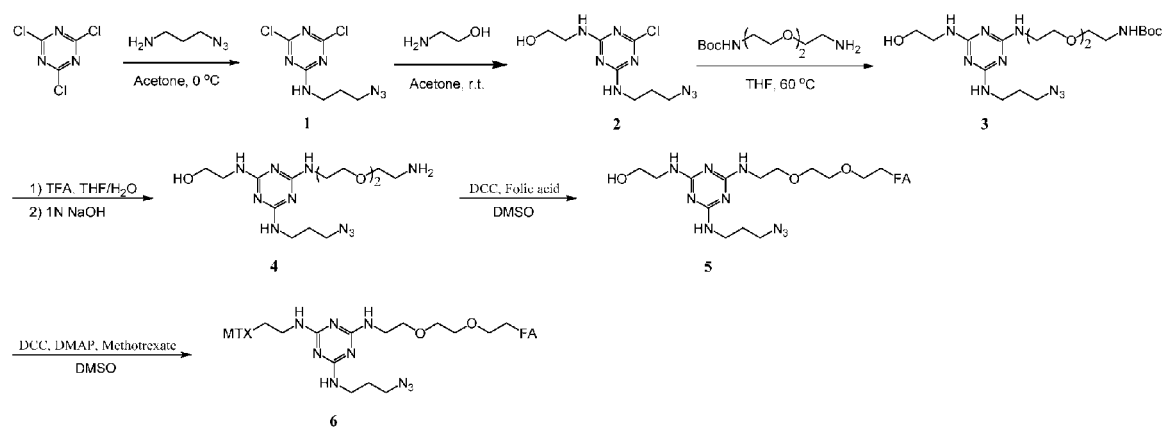
FIG. 3 shows a synthetic scheme of triazine 6.
Figure 4:
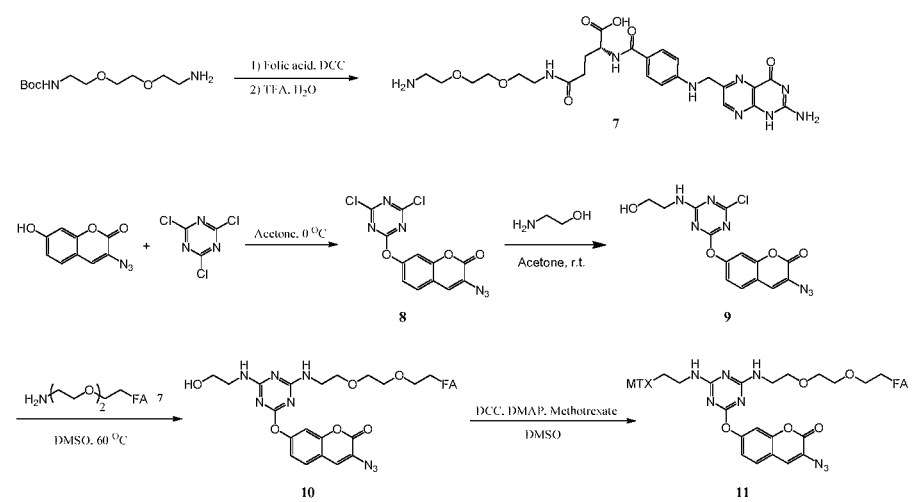
FIG. 4 shows a synthetic scheme of triazine 11.

In experiments conducted during the course of developing some embodiments of the present invention, a unique structural class 6 and 11 was developed (FIG. 1). Specifically, in some embodiments, a dendritic structure was developed which integrates bioactive molecules (e.g., FA and MTX) and a fluorophore (for 11). In these new multifunctional molecules, the trifunctional triazine was chosen as a core scaffold on which two sites could be used for binding bioactive molecules while an azide linker could be linked to its third site. High-efficiency 'click chemistry' was employed for the one-step conjugation to the alkyne terminal dendrimer (FIG. 2), which reduced the cross-linking byproducts from typical coupling reactions (Kolb et al. (2001) Angewandte Chemie-Intl. Ed. 40:2004-2021; Kolb et al. (2003) Drug Disc. Today 8:1128-1137; Lewis et al. (2002) Angewandte Chemie-Intl. Ed. 41:1053-1057; each herein incorporated by reference in its entirety). The triazine derivatives were synthesized from cyanuric chloride by consecutive aromatic nucleophilic substitution reactions under controlled conditions. Coumarine was chosen as the fluorophore due to its small size, biocompatibility, and ease of to synthetic manipulation (Sivakumar et al. (2004) Organic Lett. 6:4603-4606; herein incorporated by reference in its entirety).

Advantages of choosing triazines as substrates to build multivalent PAMAM dendrimers include but are not limited to 1) the fact that multifunctional dendrimers with targeting moiety, drug, and imaging reagent can be achieved by one-step dendrimer modification, leading to a narrow range of dendrimer molecular weights, and 2) the fact that the sequential reactivity of the three chlorine atoms in the triazine backbone makes these molecules well-suited to get high variability, useful for combinatorial synthesis. Methods and compositions of some embodiments of the present invention provide access to a novel synthetic route to multifunctional dendrimers.

Figure 9:
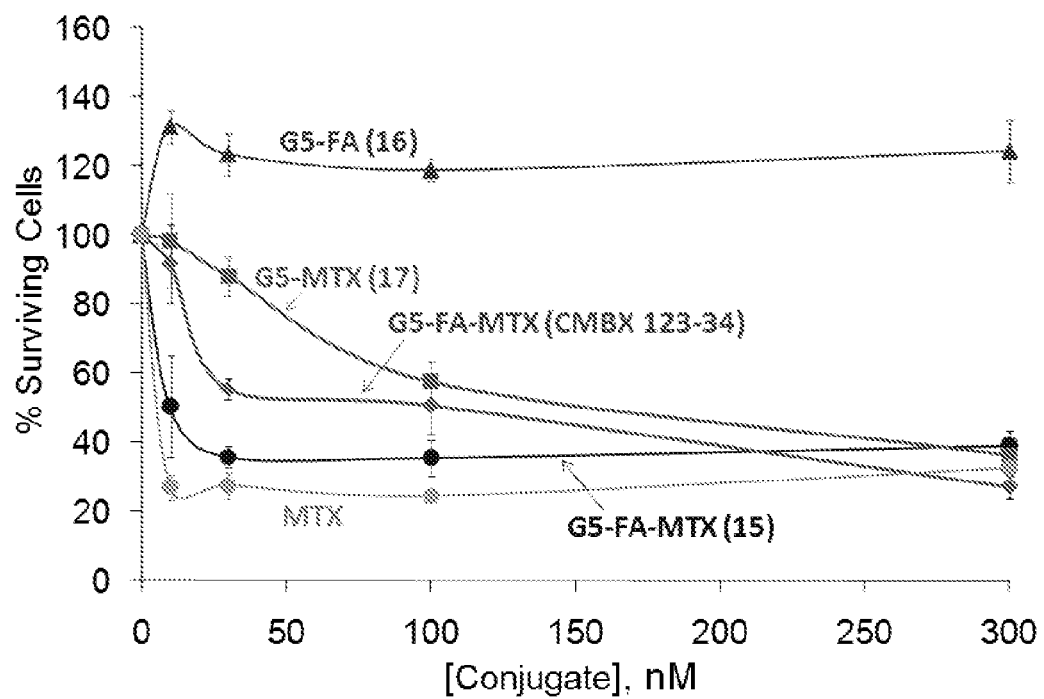
FIG. 9 shows cytotoxicity of the triazine-linked G5-conjugates G5-Triazine-αFA 16, G5-Triazine-γMTX 17 and G5-Triazine-γMTX-αFA 15. KB cells were incubated for 48 h with the indicated conjugates, the medium and drugs were then replaced with fresh medium and drugs and incubated for additional 48 h. The cytotoxicity was determined by XTT assay as given in the text. Also shown is the cytotoxicity of a previous batch of G5-FA-MTX (CMBX 123-34) containing average 4-5 FA and 7-8 MTX per dendrimer.
Figure 10:
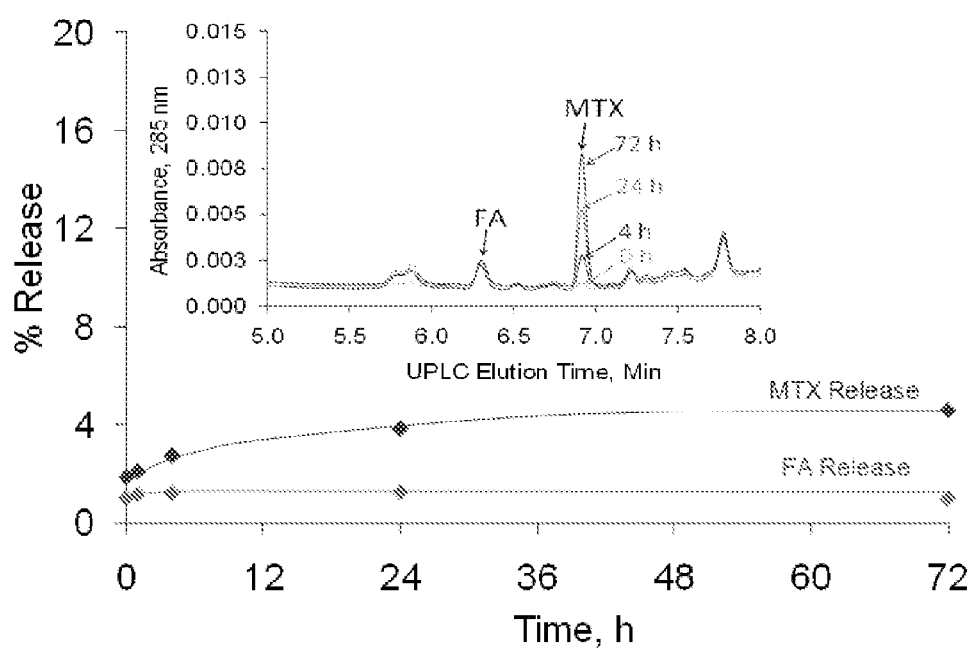
FIG. 10 shows release of free MTX and FA from G5-Triazine-γMTX-αFA conjugate 15 in cell culture medium. 15 (100 μM) was incubated with RPMI medium containing final 10% serum for different time periods and the medium proteins were precipitated with 10% DMSO in acetonitrile. The supernatant obtained were subjected HPLC analysis. The inset shows the elution peak areas of the FA and MTX. The values given on the Y-axis are expressed as the percent mole of total MTX present per mole of the dendrimer.

Moreover, experiments conducted during the course of developing some embodiments of the present invention demonstrated that such derivatives (e.g., triazine derivatives incorporating the targeting moiety FA and therapeutic drug MTX conjugated to PAMAM dendrimers through "click chemistry") demonstrated an in vitro dose-dependent cytotoxicity with higher cytotoxic potential vs. a similar conjugate synthesized by a multi-step approach (see, e.g., FIGS. 9 and 10 and Example III).

In some embodiments, the present invention provides compositions facilitating one-step (e.g., "click chemistry") conjugation of functional groups to dendrimers (e.g., terminal arms of dendrimers). In some embodiments, such compositions comprise multifunctional small molecule architectures (e.g., scaffolds) which permit conjugation to functional groups (e.g., therapeutic groups, imaging groups, targeting groups, pro-drugs complexes, trigger groups). In some embodiments, such functional group-conjugated compositions are used for one-step conjugation to dendrimers (e.g., to terminal branches of dendrimers or modified dendrimers). In some embodiments, compositions of the present invention comprise triazine compositions. In some embodiments, a triazine composition is trifunctional such that two sites are used for conjugation or binding to functional groups (e.g., bioactive molecules) and an azide linker is conjugated (e.g., linked) to the third site. Compositions of the present invention are not limited by the numerical functionality, e.g., bifunctional, trifunctional, quadfunctional or embodiments with higher degrees of are contemplated.

The present invention is not limited to the use of particular types and/or kinds of dendrimers (e.g., a dendrimer conjugated with at least one functional group). Indeed, dendrimeric polymers have been described extensively (See, e.g., Tomalia, Advanced Materials 6:529 (1994); Angew, Chem. Int. Ed. Engl., 29:138 (1990); incorporated herein by reference in their entireties). Dendrimer polymers are synthesized as defined spherical structures typically ranging from 1 to 20 nanometers in diameter. Methods for manufacturing a G5 PAMAM dendrimer with a protected core are known (U.S. patent application Ser. No. 12/403,179; herein incorporated by reference in its entirety). In preferred embodiments, the protected core diamine is $NH_2$—$CH_2$—$CH_2$—NHPG. Molecular weight and the number of terminal groups increase exponentially as a function of generation (the number of layers) of the polymer. In some embodiments of the present invention, half generation PAMAM dendrimers are used. For example, when an ethylenediamine (EDA) core is used for dendrimer synthesis, alkylation of this core through Michael addition results in a half-generation molecule with ester terminal groups; amidation of such ester groups with excess EDA results in creation of a full-generation, amine-terminated dendrimer (Majoros et al., Eds. (2008) Dendrimer-based Nanomedicine, Pan Stanford Publishing Pte. Ltd., Singapore, p. 42). Different types of dendrimers can be synthesized based on the core structure that initiates the polymerization process. In some embodiments, the PAMAM dendrimers are "Baker-Huang dendrimers" or "Baker-Huang PAMAM dendrimers" (see, e.g., U.S. Provisional Patent Application Ser. No. 61/251,244; herein incorporated by reference in its entirety).

The dendrimer core structures dictate several characteristics of the molecule such as the overall shape, density and surface functionality (See, e.g., Tomalia et al., Chem. Int. Ed.

Engl., 29:5305 (1990)). Spherical dendrimers can have ammonia as a trivalent initiator core or ethylenediamine (EDA) as a tetravalent initiator core. Recently described rod-shaped dendrimers (See, e.g., Yin et al., J. Am. Chem. Soc., 120:2678 (1998)) use polyethyleneimine linear cores of varying lengths; the longer the core, the longer the rod. Dendritic macromolecules are available commercially in kilogram quantities and are produced under current good manufacturing processes (GMP) for biotechnology applications.

Dendrimers may be characterized by a number of techniques including, but not limited to, electrospray-ionization mass spectroscopy, $^{13}$C nuclear magnetic resonance spectroscopy, $^1$H nuclear magnetic resonance spectroscopy, size exclusion chromatography with multi-angle laser light scattering, ultraviolet spectrophotometry, capillary electrophoresis and gel electrophoresis. These tests assure the uniformity of the polymer population and are important for monitoring quality control of dendrimer manufacture for GMP applications and in vivo usage.

Numerous U.S. Patents describe methods and compositions for producing dendrimers. Examples of some of these patents are given below in order to provide a description of some dendrimer compositions that may be useful in the present invention, however it should be understood that these are merely illustrative examples and numerous other similar dendrimer compositions could be used in the present invention.

U.S. Pat. No. 4,507,466, U.S. Pat. No. 4,558,120, U.S. Pat. No. 4,568,737, and U.S. Pat. No. 4,587,329 each describes methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337 describes hydrolytically stable polymers. U.S. Pat. No. 4,694,064 describes rod-shaped dendrimers. U.S. Pat. No. 4,713,975 describes dense star polymers and their use to characterize surfaces of viruses, bacteria and proteins including enzymes. Bridged dense star polymers are described in U.S. Pat. No. 4,737,550. U.S. Pat. No. 4,857,599 and U.S. Pat. No. 4,871,779 describe dense star polymers on immobilized cores useful as ion-exchange resins, chelation resins and methods of making such polymers.

U.S. Pat. No. 5,338,532 is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

U.S. Pat. No. 6,471,968 describes a dendrimer complex comprising covalently linked first and second dendrimers, with the first dendrimer comprising a first agent and the second dendrimer comprising a second agent, wherein the first dendrimer is different from the second dendrimer, and where the first agent is different than the second agent.

Other useful dendrimer type compositions are described in U.S. Pat. No. 5,387,617, U.S. Pat. No. 5,393,797, and U.S. Pat. No. 5,393,795 in which dense star polymers are modified by capping with a hydrophobic group capable of providing a hydrophobic outer shell. U.S. Pat. No. 5,527,524 discloses the use of amino terminated dendrimers in antibody conjugates.

PAMAM dendrimers are highly branched, narrowly dispersed synthetic macromolecules with well-defined chemical structures.

PAMAM dendrimers can be easily modified and conjugated with multiple functionalities such as targeting molecules, imaging agents, and drugs (Thomas et al. (2007) Poly(amidoamine) Dendrimer-based Multifunctional Nanoparticles, in Nanobiotechnology: Concepts, Methods and Perspectives, Merkin, Ed., Wiley-VCH; herein incorporated by reference in its entirety). They are water soluble, biocompatible, and cleared from the blood through the kidneys (Peer et al. (2007) Nat. Nanotechnol. 2:751-760; herein incorporated by reference in its entirety) which eliminates the need for biodegradability. Because of these desirable properties, PAMAM dendrimers have been widely investigated for drug delivery (Esfand et al. (2001) Drug Discov. Today 6:427-436; Patri et al. (2002) Curr. Opin. Chem. Biol. 6:466-471; Kukowska-Latallo et al. (2005) Cancer Res. 65:5317-5324; Quintana et al. (2002) Pharmaceutical Res. 19:1310-1316; Thomas et al. (2005) J. Med. Chem. 48:3729-3735; each herein incorporated by reference in its entirety), gene therapy (KukowskaLatallo et al. (1996) PNAS 93:4897-4902; Eichman et al. (2000) Pharm. Sci. Technolo. Today 3:232-245; Luo et al. (2002) Macromol. 35:3456-3462; each herein incorporated by reference in its entirety), and imaging applications (Kobayashi et al. (2003) Bioconj. Chem. 14:388-394; herein incorporated by reference in its entirety).

The use of dendrimers as metal ion carriers is described in U.S. Pat. No. 5,560,929. U.S. Pat. No. 5,773,527 discloses non-crosslinked polybranched polymers having a comb-burst configuration and methods of making the same. U.S. Pat. No. 5,631,329 describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

U.S. Pat. No. 5,902,863 describes dendrimer networks containing lipophilic organosilicone and hydrophilic polyanicloamine nanoscopic domains. The networks are prepared from copolydendrimer precursors having PAMAM (hydrophilic) or polyproyleneimine interiors and organosilicon outer layers. These dendrimers have a controllable size, shape and spatial distribution. They are hydrophobic dendrimers with an organosilicon outer layer that can be used for specialty membrane, protective coating, composites containing organic organometallic or inorganic additives, skin patch delivery, absorbants, chromatography personal care products and agricultural products.

U.S. Pat. No. 5,795,582 describes the use of dendrimers as adjuvants for influenza antigen. Use of the dendrimers produces antibody titer levels with reduced antigen dose. U.S. Pat. No. 5,898,005 and U.S. Pat. No. 5,861,319 describe specific immunobinding assays for determining concentration of an analyte. U.S. Pat. No. 5,661,025 provides details of a self-assembling polynucleotide delivery system comprising dendrimer polycation to aid in delivery of nucleotides to target site. This patent provides methods of introducing a polynucleotide into a eukaryotic cell in vitro comprising contacting the cell with a composition comprising a polynucleotide and a dendrimer polyeation non-covalently coupled to the polynucleotide.

Dendrimer-antibody conjugates for use in in vitro diagnostic applications have previously been demonstrated (See, e.g., Singh et al., Clin. Chem., 40:1845 (1994)), for the production of dendrimer-chelant-antibody constructs, and for the development of boronated dendrimer-antibody conjugates (for neutron capture therapy); each of these latter compounds may be used as a cancer therapeutic (See, e.g., Wu et al., Bioorg. Med. Chem. Lett., 4:449 (1994); Wiener et al., Magn. Reson. Med. 31:1 (1994); Barth et al., Bioconjugate Chem. 5:58 (1994); and Barth et al.).

Some of these conjugates have also been employed in the magnetic resonance imaging of tumors (See, e.g., Wu et al., (1994) and Wiener et al., (1994), supra). Results from this work have documented that, when administered in vivo, antibodies can direct dendrimer-associated therapeutic agents to antigen-bearing tumors. Dendrimers also have been shown to specifically enter cells and carry either chemotherapeutic agents or genetic therapeutics. In particular, studies show that cisplatin encapsulated in dendrimer polymers has increased efficacy and is less toxic than cisplatin delivered by other means (See, e.g., Duncan and Malik, Control Rel. Bioact. Mater. 23:105 (1996)).

Dendrimers have also been conjugated to fluorochromes or molecular beacons and shown to enter cells. They can then be detected within the cell in a manner compatible with sensing apparatus for evaluation of physiologic changes within cells (See, e.g., Baker et al., Anal. Chem. 69:990 (1997)). Finally, dendrimers have been constructed as differentiated block copolymers where the outer portions of the molecule may be digested with either enzyme or light-induced catalysis (See, e.g., Urdea and Hom, Science 261:534 (1993)). This allows the controlled degradation of the polymer to release therapeutics at the disease site and provides a mechanism for an external trigger to release the therapeutic agents.

In experiments conducted during the course of developing embodiments for the present invention, dendrimers containing functional components were developed having a therapeutic agent (e.g., a chemotherapeutic agent) conjugated with one or more functional groups (e.g., an imaging agent) and a targeting agent (e.g., folic acid)). The present invention is compatible with additional functional components (e.g., trigger agents (e.g., for release under hypoxic conditions)). In some embodiments, synthesis of the functionalized dendrimer is facilitated by use of triazine molecules that are linked to functional components and used for one-step (e.g., click chemistry) addition to terminal arms of dendrimers.

Accordingly, the present invention provides synthesis methods, compositions and applications for efficient, site-specific drug delivery using functionalized dendrimers comprising therapeutic agents conjugated with one or more functional groups (e.g., imaging agents, targeting agents, and trigger agents). In particular, the present invention relates to dendrimers comprising one or more functional groups conjugated with a therapeutic agent (e.g., a chemotherapeutic agent), methods of synthesizing the same, as well as systems and methods utilizing the therapeutic and diagnostic compositions (e.g., in diagnostic and/or therapeutic settings (e.g., for the delivery of therapeutics, imaging, and/or targeting agents (e.g., in disease (e.g., cancer) diagnosis and/or therapy, etc.)). For example, in some embodiments, the novel therapeutic and diagnostic compositions comprise a therapeutic agent (e.g., a chemotherapeutic agent (e.g., MTX) conjugated with an imaging agent and a targeting agent (e.g., FA). As described in more detail below, examples of functional groups include, but are not limited to, targeting groups, trigger groups, and imaging groups.

The present invention is not limited to the use of particular therapeutic agents. In some embodiments, the therapeutic agents are effective in treating autoimmune disorders and/or inflammatory disorders (e.g., arthritis). Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-α inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In some embodiments, the therapeutic agents are effective in treating cancer (see, e.g., U.S. Pat. Nos. 6,471,968, 7,078, 461, and U.S. patent application Ser. Nos. 09/940,243, 10/431,682, 11/503,742, 11/661,465, 11/523,509, 12/403, 179, 12/106,876, and 11/827,637; and U.S. Provisional Patent Application Ser. Nos. 61/256,759, 61/140,840, 61/091,608, 61/097,780, 61/101,461, 61/237,172, 61/229, 168, 61/221,596, and 61/251,244; each herein incorporated by reference in their entireties).

In some embodiments, the ligand (e.g., therapeutic agent) is conjugated with the dendrimer and/or triazine compound via a trigger agent. The present invention is not limited to particular types or kinds of trigger agents.

In some embodiments, sustained release (e.g., slow release over a period of 24-48 hours) of the ligand (e.g., therapeutic agent) is accomplished through conjugating the therapeutic agent (e.g., directly) (e.g., indirectly through one or more additional functional groups) to a trigger agent that slowly degrades in a biological system (e.g., amide linkage, ester linkage, ether linkage). In some embodiments, constitutively active release of a therapeutic agent is accomplished through conjugating the therapeutic agent to a trigger agent that renders the therapeutic agent constitutively active in a biological system (e.g., amide linkage, ether linkage).

In some embodiments, release of a therapeutic agent under specific conditions is accomplished through conjugating the therapeutic agent (e.g., directly) (e.g., indirectly through one or more additional functional groups) to a trigger agent that degrades under such specific conditions (e.g., through activation of a trigger molecule under specific conditions that leads to release of the therapeutic agent). For example, once a conjugate (e.g., a therapeutic agent conjugated with a trigger agent and a targeting agent) arrives at a target site in a subject (e.g., a tumor, or a site of inflammation), components in the target site (e.g., a tumor associated factor, or an inflammatory or pain associated factor) interact with the trigger agent thereby initiating cleavage of the therapeutic agent from the trigger agent. In some embodiments, the trigger agent is configured to degrade (e.g., release the therapeutic agent) upon exposure to a tumor-associated factor (e.g., hypoxia and pH, an enzyme (e.g., glucuronidase and/or plasmin), a cathepsin, a matrix metalloproteinase, a hormone receptor (e.g., integrin receptor, hyaluronic acid receptor, luteinizing hormone-releasing hormone receptor, etc.), cancer and/or tumor specific DNA sequence), an inflammatory associated factor (e.g., chemokine, cytokine, etc.) or other moiety.

In some embodiments, the present invention provides a therapeutic agent conjugated with a trigger agent that is sensitive to (e.g., is cleaved by) hypoxia (e.g., indolequinone).

Hypoxia is a feature of several disease states, including cancer, inflammation and rheumatoid arthritis, as well as an indicator of respiratory depression (e.g., resulting from analgesic drugs).

Advances in the chemistry of bioreductive drug activation have led to the design of various hypoxia-selective drug delivery systems in which the pharmacophores of drugs are masked by reductively cleaved groups. In some embodiments, the trigger agent is utilizes a quinone, N-oxide and/or (hetero)aromatic nitro groups. For example, a quinone present in a conjugate is reduced to phenol under hypoxia conditions, with spontaneous formation of lactone that serves as a driving force for drug release. In some embodiments, a heteroaromatic nitro compound present in a conjugate (e.g., a therapeutic agent conjugated (e.g., directly or indirectly) with a trigger agent) is reduced to either an amine or a hydroxylamine, thereby triggering the spontaneous release of a therapeutic agent. In some embodiments, the trigger agent degrades upon detection of reduced pO2 concentrations (e.g., through use of a redox linker).

The concept of pro-drug systems in which the pharmacophores of drugs are masked by reductively cleavable groups has been widely explored by many research groups and pharmaceutical companies (see, e.g., Beall, H. D., et al., Journal of Medicinal Chemistry, 1998. 41(24): p. 4755-4766; Ferrer, S., D. P. Naughton, and M. D. Threadgill, Tetrahedron, 2003. 59(19): p. 3445-3454; Naylor, M. A., et al., Journal of Medicinal Chemistry, 1997. 40(15): p. 2335-2346; Phillips, R. M., et al., Journal of Medicinal Chemistry, 1999. 42(20): p. 4071-4080; Zhang, Z., et al., Organic & Biomolecular Chemistry, 2005. 3(10): p. 1905-1910; each of which are herein incorporated by reference in their entireties). Several such hypoxia activated pro-drugs have been advanced to clinical investigations, and work in relevant oxygen concentrations to prevent cerebral damage. The present invention is not limited to particular hypoxia activated trigger agents. In some embodiments, the hypoxia activated trigger agents include, but are not limited to, indolequinones, nitroimidazoles, and nitroheterocycles (see, e.g., Damen, E. W. P., et al., Bioorganic & Medicinal Chemistry, 2002. 10(1): p. 71-77; Hay, M. P., et al., Journal of Medicinal Chemistry, 2003. 46(25): p. 5533-5545; Hay, M. P., et al., Journal of the Chemical Society-Perkin Transactions 1, 1999(19): p. 2759-2770; each herein incorporated by reference in their entireties).

In some embodiments, the trigger agent is sensitive to (e.g., is cleaved by) and/or associates with a tumor-associated enzyme. For example, in some embodiments, the trigger agent that is sensitive to (e.g., is cleaved by) and/or associates with a glucuronidase. Glucuronic acid can be attached to several anticancer drugs via various linkers. These anticancer drugs include, but are not limited to, doxorubicin, paclitaxel, docetaxel, 5-fluorouracil, 9-aminocamtothecin, as well as other drugs under development. These pro-drugs are generally stable at physiological pH and are significantly less toxic than the parent drugs.

In some embodiments, the trigger agent is sensitive to (e.g., is cleaved by) and/or associates with brain enzymes. For example, trigger agents such as indolequinone are reduced by brain enzymes such as, for example, diaphorase (DT-diaphorase) (see, e.g., Damen, E. W. P., et al., Bioorganic & Medicinal Chemistry, 2002. 10(1): p. 71-77; herein incorporated by reference in its entirety). For example, in such embodiments, the antagonist is only active when released during hypoxia to prevent respiratory failure.

In some embodiments, the trigger agent is sensitive to (e.g., is cleaved by) and/or associates with a protease. The present invention is not limited to any particular protease. In some embodiments, the protease is a cathepsin. In some embodiments, a trigger comprises a Lys-Phe-PABC moiety (e.g., that acts as a trigger). In some embodiments, a Lys-Phe-PABC moiety linked to doxorubicin, mitomycin C, and paclitaxel are utilized as a trigger-therapeutic conjugate in a dendrimer conjugate provided herein (e.g., that serve as substrates for lysosomal cathepsin B or other proteases expressed (e.g., overexpressed) in tumor cells. In some embodiments, utilization of a 1,6-elimination spacer/linker is utilized (e.g., to permit release of therapeutic drug post activation of trigger).

In some embodiments, the trigger agent is sensitive to (e.g., is cleaved by) and/or associates with plasmin. The serine protease plasmin is over expressed in many human tumor tissues. Tripeptide specifiers (e.g., including, but not limited to, Val-Leu-Lys) have been identified and linked to anticancer drugs through elimination or cyclization linkers.

In some embodiments, the trigger agent is sensitive to (e.g., is cleaved by) and/or associates with a matrix metalloprotease (MMP). In some embodiments, the trigger agent is sensitive to (e.g., is cleaved by) and/or that associates with β-Lactamase (e.g., a β-Lactamase activated cephalosporin-based pro-drug).

In some embodiments, the trigger agent is sensitive to (e.g., is cleaved by) and/or activated by a receptor (e.g., expressed on a target cell (e.g., a tumor cell)).

In some embodiments, the trigger agent is sensitive to (e.g., is cleaved by) and/or activated by a nucleic acid. Nucleic acid triggered catalytic drug release can be utilized in the design of chemotherapeutic agents. Thus, in some embodiments, disease specific nucleic acid sequence is utilized as a drug releasing enzyme-like catalyst (e.g., via complex formation with a complimentary catalyst-bearing nucleic acid and/or analog). In some embodiments, the release of a therapeutic agent is facilitated by the therapeutic component being attached to a labile protecting group, such as, for example, cisplatin or methotrexate being attached to a photolabile protecting group that becomes released by laser light directed at cells emitting a color of fluorescence (e.g., in addition to and/or in place of target activated activation of a trigger component of a dendrimer conjugate). In some embodiments, the therapeutic device also may have a component to monitor the response of the tumor to therapy. For example, where a therapeutic agent of the dendrimer induces apoptosis of a target cell (e.g., a cancer cell (e.g., a prostate cancer cell)), the caspase activity of the cells may be used to activate a green fluorescence. This allows apoptotic cells to turn orange, (combination of red and green) while residual cells remain red. Any normal cells that are induced to undergo apoptosis in collateral damage fluoresce green.

In some embodiments, a dendrimer is conjugated (e.g., directly or indirectly (e.g., via a triazine compound)) with a targeting agent. The present invention is not limited to any particular targeting agent. In some embodiments, targeting agents are conjugated to a dendrimer (eg., directly or indirectly) for delivery to desired body regions (e.g., to the central nervous system (CNS); to a tumor). The targeting agents are not limited to targeting specific body regions.

In some embodiments, the targeting agent is a moiety that has affinity for a tumor associated factor. For example, a number of targeting agents are contemplated to be useful in the present invention including, but not limited to, RGD sequences, low-density lipoprotein sequences, a NAALA-Dase inhibitor, epidermal growth factor, and other agents that bind with specificity to a target cell (e.g., a cancer cell)).

The present invention is not limited to cancer and/or tumor targeting agents. Indeed, multifunctional dendrimers can be targeted (e.g., via a linker conjugated to the dendrimer wherein the linker comprises a targeting agent) to a variety of target cells or tissues (e.g., to a biologically relevant environment) via conjugation to an appropriate targeting agent. For example, in some embodiments, the targeting agent is a moiety that has affinity for an inflammatory factor (e.g., a cytokine or a cytokine receptor moiety (e.g., TNF-α receptor)). In some embodiments, the targeting agent is a sugar, peptide, antibody or antibody fragment, hormone, hormone receptor, or the like.

In some embodiments of the present invention, the targeting agent includes, but is not limited to an antibody, receptor ligand, hormone, vitamin, and antigen, however, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some embodiments, the targeting agent is an antibody. In some embodiments, the antibodies recognize, for example, tumor-specific epitopes (e.g., TAG-72 (See, e.g., Kjeldsen et al., Cancer Res. 48:2214-2220 (1988); U.S. Pat. Nos. 5,892, 020; 5,892,019; and 5,512,443; each herein incorporated by reference in their entireties); human carcinoma antigen (See, e.g., U.S. Pat. Nos. 5,693,763; 5,545,530; and 5,808,005; each herein incorporated by reference in their entireties); TP1 and TP3 antigens from osteocarcinoma cells (See, e.g., U.S. Pat. No. 5,855,866; herein incorporated by reference in its entirety); Thomsen-Friedenreich (TF) antigen from adenocarcinoma cells (See, e.g., U.S. Pat. No. 5,110,911; herein incorporated by reference in its entirety); "KC-4 antigen" from human prostrate adenocarcinoma (See, e.g., U.S. Pat. Nos. 4,708,930 and 4,743,543; each herein incorporated by reference in their entireties); a human colorectal cancer antigen (See, e.g., U.S. Pat. No. 4,921,789; herein incorporated by reference in its entirety); CA125 antigen from cystadenocarcinoma (See, e.g., U.S. Pat. No. 4,921,790; herein incorporated by reference in its entirety); DF3 antigen from human breast carcinoma (See, e.g., U.S. Pat. Nos. 4,963,484 and 5,053,489; each herein incorporated by reference in their entireties); a human breast tumor antigen (See, e.g., U.S. Pat. No. 4,939,240: herein incorporated by reference in its entirety); p97 antigen of human melanoma (See, e.g., U.S. Pat. No. 4,918,164: herein incorporated by reference in its entirety); carcinoma or orosomucoid-related antigen (CORA) (See, e.g., U.S. Pat. No. 4,914,021; herein incorporated by reference in its entirety); a human pulmonary carcinoma antigen that reacts with human squamous cell lung carcinoma but not with human small cell lung carcinoma (See, e.g., U.S. Pat. No. 4,892,935; herein incorporated by reference in its entirety); T and Tn haptens in glycoproteins of human breast carcinoma (See, e.g., Springer et al., Carbohydr. Res. 178:271-292 (1988); herein incorporated by reference in its entirety), MSA breast carcinoma glycoprotein termed (See, e.g., Tjandra et al., Br. J. Surg. 75:811-817 (1988); herein incorporated by reference in its entirety); MFGM breast carcinoma antigen (See, e.g., Ishida et al., Tumor Biol. 10:12-22 (1989); herein incorporated by reference in its entirety); DU-PAN-2 pancreatic carcinoma antigen (See, e.g., Lan et al., Cancer Res. 45:305-310 (1985); herein incorporated by reference in its entirety); CA125 ovarian carcinoma antigen (See, e.g., Hanisch et al., Carbohydr. Res. 178:29-47 (1988); herein incorporated by reference in its entirety);YH206 lung carcinoma antigen (See, e.g., Hinoda et al., (1988) Cancer J. 42:653-658 (1988); herein incorporated by reference in its entirety).

In some embodiments, the targeting agents target the central nervous system (CNS). In some embodiments, where the targeting agent is specific for the CNS, the targeting agent is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). Transferrin has been utilized as a targeting vector to transport, for example, drugs, liposomes and proteins across the blood-brain barrier (BBB) by receptor mediated transcytosis (see, e.g., Smith, M. W. and M. Gumbleton, Journal of Drug Targeting, 2006. 14(4): p. 191-214; herein incorporated by reference in its entirety). In some embodiments, the targeting agents target neurons within the central nervous system (CNS). In some embodiments, where the targeting agent is specific for neurons within the CNS, the targeting agent is a synthetic tetanus toxin fragment (e.g., a 12 amino acid peptide (Tet 1) (HLNILSTL-WKYR) (SEQ ID NO: 2)) (see, e.g., Liu, J. K., et al., Neurobiology of Disease, 2005. 19(3): p. 407-418; herein incorporated by reference in its entirety).

In some embodiments, a dendrimer is conjugated (e.g., directly or indirectly (e.g., via a triazine compound)) to an imaging agent. A multiplicity of imaging agents find use in the present invention. In some embodiments, a multifunctional dendrimer comprises at least one imaging agent that can be readily imaged. The present invention is not limited by the nature of the imaging component used. In some embodiments of the present invention, imaging modules comprise surface modifications of quantum dots (See e.g., Chan and Nie, Science 281:2016 (1998)) such as zinc sulfide-capped cadmium selenide coupled to biomolecules (Sooklal, Adv. Mater., 10:1083 (1998)).

In some embodiments, once a component(s) of a targeted multifunctional dendrimer has attached to (or been internalized into) a target cell (e.g., tumor cell and or inflammatory cell), one or more modules on serves to image its location. In some embodiments, chelated paramagnetic ions, such as Gd(III)-diethylenetriaminepentaacetic acid (Gd(III)-DTPA), are conjugated to the multifunctional dendrimer. Other paramagnetic ions that may be useful in this context include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof.

Dendrimeric gadolinium contrast agents have even been used to differentiate between benign and malignant breast tumors using dynamic MRI, based on how the vasculature for the latter type of tumor images more densely (Adam et al., Ivest. Rad. 31:26 (1996)). Thus, MRI provides a particularly useful imaging system of the present invention.

Multifunctional dendrimers allow functional microscopic imaging of tumors and provide improved methods for imaging. The methods find use in vivo, in vitro, and ex vivo. For example, in one embodiment, dendrimer functional groups are designed to emit light or other detectable signals upon exposure to light. Although the labeled functional groups may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (See, e.g., Farkas et al., SPEI 2678: 200 (1997); herein incorporated by reference in its entirety). In embodiments where the imaging agents are present in deeper tissue, longer wavelengths in the Near-infrared (NMR) are used (See e.g., Lester et al., Cell Mol. Biol. 44:29 (1998); herein incorporated by reference in its entirety). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce when excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. For example, in some embodiments, biosensor-comprising pro-drug complexes are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic biosensors for pH, oxygen concentration, $Ca^{2+}$ concentration, and other physiologically relevant analytes.

In some embodiments, the present invention provides multifunctional dendrimers (e.g., conjugated with a triazine compound) having a biological monitoring component. The biological monitoring or sensing component of a multifunctional dendrimer is one that can monitor the particular response in a target cell (e.g., tumor cell) induced by an agent (e.g., a therapeutic agent provided by a multifunctional dendrimer). While the present invention is not limited to any particular monitoring system, the invention is illustrated by methods and compositions for monitoring cancer treatments. In preferred embodiments of the present invention, the agent induces apoptosis in cells and monitoring involves the detection of apoptosis. In some embodiments, the monitoring component is an agent that fluoresces at a particular wavelength when apoptosis occurs. For example, in a preferred embodiment, caspase activity activates green fluorescence in the monitoring component. Apoptotic cancer cells, which have turned red as a result of being targeted by a particular signature with a red label, turn orange while residual cancer cells remain red. Normal cells induced to undergo apoptosis (e.g., through collateral damage), if present, will fluoresce green.

In these embodiments, fluorescent groups such as fluorescein are employed in the imaging agent. Fluorescein is easily attached to the dendrimer surface via the isothiocyanate derivatives, available from MOLECULAR PROBES, Inc. This allows the multifunctional dendrimer or components thereof to be imaged with the cells via confocal microscopy. Sensing of the effectiveness of the multifunctional dendrimer or components thereof is preferably achieved by using fluorogenic peptide enzyme substrates. For example, apoptosis caused by the therapeutic agent results in the production of the peptidase caspase-1 (ICE). CALBIOCHEM sells a number of peptide substrates for this enzyme that release a fluorescent moiety. A particularly useful peptide for use in the present invention is: MCA-Tyr-Glu-Val-Asp-Gly-Trp-Lys-(DNP)-NH$_2$ (SEQ ID NO: 1) where MCA is the (7-methoxycoumarin-4-yl)acetyl and DNP is the 2,4-dinitrophenyl group (See, e.g., Talanian et al., J. Biol. Chem., 272: 9677 (1997); herein incorporated by reference in its entirety). In this peptide, the MCA group has greatly attenuated fluorescence, due to fluorogenic resonance energy transfer (FRET) to the DNP group. When the enzyme cleaves the peptide between the aspartic acid and glycine residues, the MCA and DNP are separated, and the MCA group strongly fluoresces green (excitation maximum at 325 nm and emission maximum at 392 nm). In some embodiments, the lysine end of the peptide is linked to pro-drug complex, so that the MCA group is released into the cytosol when it is cleaved. The lysine end of the peptide is a useful synthetic handle for conjugation because, for example, it can react with the activated ester group of a bifunctional linker such as Mal-PEG-OSu. Thus the appearance of green fluorescence in the target cells produced using these methods provides a clear indication that apoptosis has begun (if the cell already has a red color from the presence of aggregated quantum dots, the cell turns orange from the combined colors).

Additional fluorescent dyes that find use with the present invention include, but are not limited to, acridine orange, reported as sensitive to DNA changes in apoptotic cells (see, e.g., Abrams et al., Development 117:29 (1993); herein incorporated by reference in its entirety) and cis-parinaric acid, sensitive to the lipid peroxidation that accompanies apoptosis (see, e.g., Hockenbery et al., Cell 75:241 (1993); herein incorporated by reference in its entirety). It should be noted that the peptide and the fluorescent dyes are merely exemplary. It is contemplated that any peptide that effectively acts as a substrate for a caspase produced as a result of apoptosis finds use with the present invention.

In some embodiments, conjugation between a dendrimer (e.g., terminal arm of a dendrimer) and a functional group or between functional groups is accomplished through use of a 1,3-dipolar cycloaddition reaction ("click chemistry"). Moreover, in some embodiments, conjugation between a dendrimer (e.g., terminal arm of a dendrimer) and a triazine compound (e.g.,

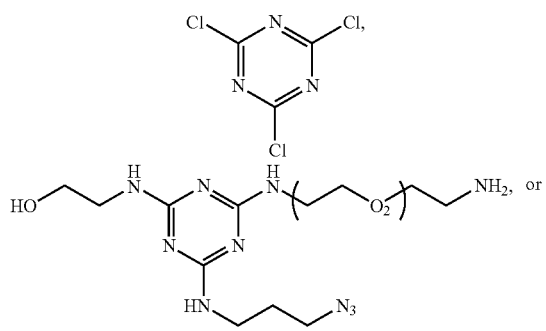

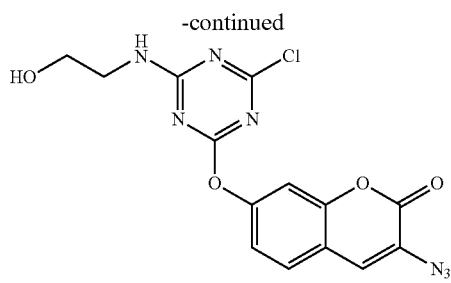

is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (e.g., present on a triazine composition of the present invention) (or equivalent thereof) (or any active end group such as, for example, a primary amine end group, a hydroxyl end group, a carboxylic acid end group, a thiol end group, etc.) on the second moiety. 'Click chemistry' is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

In some embodiments, conjugation between a dendrimer (e.g., a terminal arm of a dendrimer) and a functional ligand is accomplished during a "one-pot" reaction. The term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants. In some embodiments, a one-pot reaction occurs wherein a hydroxyl-terminated dendrimer (e.g., HO-PAMAM dendrimer) is reacted with one or more functional ligands (e.g., a therapeutic agent, a pro-drug, a trigger agent, a targeting agent, an imaging agent) in one vessel, such conjugation being facilitated by ester coupling agents (e.g., 2-chloro-1-methylpyridinium iodide and 4-(dimethylamino) pyridine) (see, e.g., International Patent Application No. PCT/US2010/042556, herein incorporated by reference in its entirety).

Functionalized nanoparticles (e.g., dendrimers) often contain moieties (including but not limited to ligands, functional ligands, conjugates, therapeutic agents, targeting agents, imaging agents, fluorophores) that are conjugated to the periphery. Such moieties may for example be conjugated to one or more dendrimer branch termini. Classical multi-step conjugation strategies used during the synthesis of functionalized dendrimers generate a stochastic distribution of products with differing numbers of ligands attached per dendrimer molecule, thereby creating a population of dendrimers with a wide distribution in the numbers of ligands attached. The low structural uniformity of such dendrimer populations negatively affects properties such as therapeutic potency, pharmacokinetics, or effectiveness for multivalent targeting. Difficulties in quantifying and resolving such populations to yield samples with sufficient structural uniformity can pose challenges. However, in some embodiments, use of separation methods (e.g., reverse phase chromatography) customized for optimal separation of dendrimer populations in conjunction with peak fitting analysis methods allows isolation and identification of subpopulations of functionalized dendrimers with high structural uniformity (see, e.g., U.S. Provisional Pat. App. No. 61/237,172; herein incorporated by reference in its entirety). In certain embodiments, such methods and systems provide a dendrimer product made by the process comprising: a) conjugation of at least one ligand type to a dendrimer to yield a population of ligand-conjugated dendrimers; b) separation of the population of ligand-conjugated dendrimers with reverse phase HPLC to result in subpopulations of ligand-conjugated dendrimers indicated by a chromatographic trace; and c) application of peak fitting analysis to the chromatographic trace to identify subpopulations of ligand-conjugated dendrimers wherein the structural uniformity of ligand conjugates per molecule of dendrimer within said subpopulation is, e.g., approximately 80% or more.

The present invention is not limited by the type of therapeutic agent delivered via multifunctional dendrimers of the present invention. For example, a therapeutic agent may be any agent selected from the group comprising, but not limited to, a pain relief agent, a pain relief agent antagonist, a chemotherapeutic agent, an anti-oncogenic agent, an anti-angiogenic agent, a tumor suppressor agent, an anti-microbial agent, or an expression construct comprising a nucleic acid encoding a therapeutic protein.

Indeed, in some embodiments of the present invention, methods and compositions are provided for the treatment of inflammatory diseases (e.g., dendrimers conjugated with therapeutic agents configured for treating inflammatory diseases). Inflammatory diseases include but are not limited to arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

In some embodiments, the conjugated dendrimers of the present invention configured for treating autoimmune disorders and/or inflammatory disorders (e.g., rheumatoid arthritis) are co-administered to a subject (e.g., a human suffering from an autoimmune disorder and/or an inflammatory disorder) with a therapeutic agent configured for treating autoimmune disorders and/or inflammatory disorders (e.g., rheumatoid arthritis). Examples of such agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone), IL-1 inhibitors, and metalloprotease inhibitors.

In some embodiments, the medical condition and/or disease is pain (e.g., chronic pain, mild pain, recurring pain, severe pain, etc.). In some embodiments, the conjugated dendrimers of the present invention are configured to deliver pain relief agents to a subject (see, e.g., U.S. patent application Ser. No. 12/570,977; herein incorporated by reference in its entirety). In some embodiments, the dendrimer conjugates are configured to deliver pain relief agents and pain relief agent antagonists to counter the side effects of pain relief agents (see, e.g., U.S. patent application Ser. No. 12/570,977; herein incorporated by reference in its entirety). The dendrimer conjugates are not limited to treating a particular type of pain and/or pain resulting from a disease (see, e.g., U.S. patent application Ser. No. 12/570,977; herein incorporated by reference in its entirety). Examples include, but are not limited to, pain resulting from trauma (e.g., trauma experienced on a battlefield, trauma experienced in an accident (e.g., car accident)). In some embodiments, the dendrimer conjugates of the present invention are configured such that they are readily cleared from the subject (e.g., so that there is little to no detectable toxicity at efficacious doses) (see, e.g., U.S. patent application Ser. No. 12/570,977; herein incorporated by reference in its entirety).

In some embodiments, the disease is cancer. The present invention is not limited by the type of cancer treated using the compositions and methods of the present invention. Indeed, a variety of cancer can be treated including, but not limited to, prostate cancer, colon cancer, breast cancer, lung cancer and epithelial cancer.

In some embodiments, the disease is a neoplastic disease, selected from, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma. In some embodiments, the disease is an inflammatory disease selected from the group consisting of, but not limited to, eczema, inflammatory bowel disease, rheumatoid arthritis, asthma, psoriasis, ischemia/reperfusion injury, ulcerative colitis and acute respiratory distress syndrome. In some embodiments, the disease is a viral disease selected from the group consisting of, but not limited to, viral disease caused by hepatitis B, hepatitis C, rotavirus, human immunodeficiency virus type I (HIV-I), human immunodeficiency virus type II (HIV-II), human T-cell lymphotropic virus type I (HTLV-I), human T-cell lymphotropic virus type II (HTLV-II), AIDS, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

In some embodiments, the dendrimer is conjugated with one or more anti-cancer agents. In some embodiments, the dendrimer is co-administered with one or more anti-cancer agents. Examples of anti-cancer agents include, but are not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda). Other anti-cancer agents include, but are not limited to, Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131.

Additional anti-cancer agents include, but are not limited to anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. Still other anticancer agents include, but are not limited to, annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2'-deoxyadenosine; Fludarabine-$PO_4$; mitoxantrone; mitozolomide; Pentostatin; and Tomudex. One particularly preferred class of anticancer agents are taxanes (e.g., paclitaxel and docetaxel). Another important category of anticancer agent is annonaceous acetogenin.

In some embodiments, the dendrimer is conjugated with one or more pain relief agents. In some embodiments, the dendrimer is co-administered with one or more pain relief agents. In some embodiments, the pain relief agents include, but are not limited to, analgesic drugs, anxiolytic drugs, anesthetic drugs, antipsychotic drugs, hypnotic drugs, sedative drugs, and muscle relaxant drugs (see, e.g., U.S. patent application Ser. No. 12/570,977; herein incorporated by reference in its entirety).

In some embodiments, the analgesic drugs include, but are not limited to, non-steroidal anti-inflammatory drugs, COX-2 inhibitors, and opiates. In some embodiments, the non-steroidal anti-inflammatory drugs are selected from the group consisting of Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate, Salicylamide, arylalkanoic acids, Diclofenac, Aceclofenac, Acemetharcin, Alclofenac, Bromfenac, Etodolac, Indometacin, Nabumetone, Oxametacin, Proglumetacin, Sulindac, Tolmetin, 2-arylpropionic acids, Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids, Mefenamic acid, Flufenamic acid, Meclofenamic acid, Tolfenamic acid, pyrazolidine derivatives, Phenylbutazone, Ampyrone, Azapropazone, Clofezone, Kebuzone, Metamizole, Mofebutazone, Oxyphenbutazone, Phenazone, Sulfinpyrazone, oxicams, Piroxicam, Droxicam, Lornoxicam, Meloxicam, Tenoxicam, sulphonanilides, nimesulide, licofelone, and omega-3 fatty acids. In some embodiments, the COX-2 inhibitors are selected from the group consisting of Celecoxib, Etoricoxib, Lumiracoxib, Parecoxib, Rofecoxib, and Valdecoxib. In some embodiments, the opiate drugs are selected from the group consisting of natural opiates, alkaloids, morphine, codeine, thebaine, semi-synthetic opiates, hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, ethylmorphine, fully synthetic opioids, fentanyl, pethidine, Oxycodone, Oxymorphone, methadone, tramadol, Butorphanol, Levorphanol, propoxyphene, endogenous opioid peptides, endorphins, enkephalins, dynorphins, and endomorphins.

In some embodiments, the anxiolytic drugs include, but are not limited to, benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze, Triazolam, serotonin 1A agonists, Buspirone (BuSpar), barbituates, amobarbital (Amytal), pentobarbital (Nembutal), secobarbital (Seconal), Phenobarbital, Methohexital, Thiopental, Methylphenobarbital, Metharbital, Barbexaclone), hydroxyzine, cannabidiol, valerian, kava (Kava Kava), chamomile, Kratom, Blue Lotus extracts, Sceletium tortuosum (kanna) and bacopa monniera.

In some embodiments, the anesthetic drugs include, but are not limited to, local anesthetics, procaine, amethocaine, cocaine, lidocaine, prilocalne, bupivacaine, levobupivacaine, ropivacaine, dibucaine, inhaled anesthetics, Desflurane, Enflurane, Halothane, Isoflurane, Nitrous oxide, Sevoflurane, Xenon, intravenous anesthetics, Barbiturates, amobarbital (Amytal), pentobarbital (Nembutal), secobarbital (Seconal), Phenobarbital, Methohexital, Thiopental, Methylphenobarbital, Metharbital, Barbexaclone)), Benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam, Etomidate, Ketamine, and Propofol.

In some embodiments, the antipsychotic drugs include, but are not limited to, butyrophenones, haloperidol, phenothiazines, Chlorpromazine (Thorazine), Fluphenazine (Prolixin), Perphenazine (Trilafon), Prochlorperazine (Compazine), Thioridazine (Mellaril), Trifluoperazine (Stelazine), Mesoridazine, Promazine, Triflupromazine (Vesprin), Levomepromazine (Nozinan), Promethazine (Phenergan)), thioxanthenes, Chlorprothixene, Flupentixol (Depixol and Fluanxol), Thiothixene (Navane), Zuclopenthixol (Clopixol & Acuphase)), clozapine, olanzapine, Risperidone (Risperdal), Quetiapine (Seroquel), Ziprasidone (Geodon), Amisulpride (Solian), Paliperidone (Invega), dopamine, bifeprunox, norclozapine (ACP-104), Aripiprazole (Abilify), Tetrabenazine, and Cannabidiol.

In some embodiments, the hypnotic drugs include, but are not limited to, Barbiturates, Opioids, benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam, nonbenzodiazepines, Zolpidem, Zaleplon, Zopiclone, Eszopiclone, antihistamines, Diphenhydramine, Doxylamine, Hydroxyzine, Promethazine, gamma-hydroxybutyric acid (Xyrem), Glutethimide, Chloral hydrate, Ethchlorvynol, Levomepromazine, Chlormethiazole, Melatonin, and Alcohol.

In some embodiments, the sedative drugs include, but are not limited to, barbituates, amobarbital (Amytal), pentobarbital (Nembutal), secobarbital (Seconal), Phenobarbital, Methohexital, Thiopental, Methylphenobarbital, Metharbital, Barbexaclone), benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam, herbal sedatives, ashwagandha, catnip, kava (*Piper methysticum*), mandrake, marijuana, valerian, solvent sedatives, chloral hydrate (Noctec), diethyl ether (Ether), ethyl alcohol (alcoholic beverage), methyl trichloride (Chloroform), nonbenzodiazepine sedatives, eszopiclone (Lunesta), zaleplon (Sonata), zolpidem (Ambien), zopiclone (Imovane, Zimovane)), clomethiazole (clomethiazole), gamma-hydroxybutyrate (GHB), Thalidomide, ethchlorvynol (Placidyl), glutethimide (Doriden), ketamine (Ketalar, Ketaset), methaqualone (Sopor, Quaalude), methyprylon (Noludar), and ramelteon (Rozerem).

In some embodiments, the muscle relaxant drugs include, but are not limited to, depolarizing muscle relaxants, Succinylcholine, short acting non-depolarizing muscle relaxants, Mivacurium, Rapacuronium, intermediate acting non-depolarizing muscle relaxants, Atracurium, Cisatracurium, Rocuronium, Vecuronium, long acting non-depolarizing muscle relaxants, Alcuronium, Doxacurium, Gallamine, Metocurine, Pancuronium, Pipecuronium, and d-Tubocurarine.

In some embodiments, the dendrimer is conjugated with one or more pain relief agent antagonists. In some embodiments, the dendrimer is co-administered with one or more pain relief agent antagonists (see, e.g., U.S. patent application Ser. No. 12/570,977; herein incorporated by reference in its entirety).

In some embodiments, the pain relief agent antagonists include drugs that counter the effect of a pain relief agent (e.g., an anesthetic antagonist, an analgesic antagonist, a mood stabilizer antagonist, a psycholeptic drug antagonist, a psychoanaleptic drug antagonist, a sedative drug antagonist, a muscle relaxant drug antagonist, and a hypnotic drug antagonist). In some embodiments, pain relief agent antagonists include, but are not limited to, a respiratory stimulant, Doxapram, BIMU-8, CX-546, an opiod receptor antagonist, Naloxone, naltrexone, nalorphine, levallorphan, cyprodime, naltrindole, norbinaltorphimine, buprenorphine, a benzodiazepine antagonist, flumazenil, a non-depolarizing muscle relaxant antagonist, and neostigmine.

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein.

In preferred embodiments, the dendrimer conjugates are used in conjunction with appropriate salts and buffers to render delivery of the compositions in a stable manner to allow for uptake by target cells. Buffers also are employed when the dendrimer conjugates are introduced into a patient. Aqueous compositions comprise an effective amount of the dendrimer conjugates to cells dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with vectors, cells, or tissues, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active dendrimer conjugates may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some embodiments, a therapeutic agent is released from dendrimer conjugates within a target cell (e.g., within an endosome). This type of intracellular release (e.g., endosomal disruption of a linker-therapeutic conjugate) is contemplated to provide additional specificity for the compositions and methods of the present invention. The present invention provides dendrimers with multiple (e.g., 100-150) reactive sites for the conjugation of linkers and/or functional groups comprising, but not limited to, therapeutic agents, targeting agents, imaging agents and biological monitoring agents.

The compositions and methods of the present invention are contemplated to be equally effective whether or not the dendrimer conjugates of the present invention comprise a fluorescein (e.g. FITC) imaging agent. Thus, each functional group present in a dendrimer composition is able to work independently of the other functional groups. Thus, the present invention provides dendrimer conjugates that can comprise multiple combinations of targeting, therapeutic, imaging, and biological monitoring functional groups.

The present invention also provides a very effective and specific method of delivering molecules (e.g., therapeutic and imaging functional groups) to the interior of target cells (e.g., cancer cells). Thus, in some embodiments, the present invention provides methods of therapy that comprise or require delivery of molecules into a cell in order to function (e.g., delivery of genetic material such as siRNAs).

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, dendrimer conjugates are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. In addition, suppositories may be used in connection with colon cancer. The dendrimer conjugates also may be formulated as inhalants for the treatment of lung cancer and such like.

In some embodiments, the present invention also provides kits comprising one or more of the reagents and tools necessary to generate a dendrimer conjugated with one or more triazine compositions (e.g., scaffolds) (e.g., triazine compositions capable of click chemistry for use in one-step synthesis of functionalized dendrimers) (e.g., triazine compositions having one or more functional groups), and methods of using such dendrimers.

EXAMPLES

The following examples are provided in order to demonstrate and further illustrate certain preferred embodiments and aspects of the present invention and are not to be construed as limiting the scope thereof.

Example 1

Previous experiments involving dendrimer related technologies are located in U.S. Pat. Nos. 6,471,968, 7,078,461; U.S. patent application Ser. Nos. 09/940,243, 10/431,682, 11/503,742, 11,661,465, 11/523,509, 12/403,179, 12/106, 876, 11/827,637, 10/039,393, 10/254,126, 09/867,924, 12/570,977, and 12/645,081; U.S. Provisional Patent Application Ser. Nos. 61/140,480, 61/091,608, 61/097,780, 61/101,461, 61/251,244, 60/604,321, 60/690,652, 60/707, 991, 60/208,728, 60/718,448, 61/035,949, 60/830,237, and 60/925,181; and International Patent Application Nos. PCT/US2010/042556, PCT/US2001/015204, PCT/US2005/030278, PCT/US2009/069257, PCT/US2009/036992, PCT/US2009/059071, PCT/US2007/015976, and PCT/US2008/061023, each herein incorporated by reference in their entireties.

Example 2

Clickable Multifunctional Small Molecules for Surface Functionalization of PAMAM Dendrimer General Information

[1] $^1$H NMR spectra were obtained using a Varian Inova 500 MHz spectrometer. Matrix-assisted laser desorption ionization time-of-flight mass spectra (MALDI-TOF-MS) were recorded on a PE Biosystems Voyager System 6050, using α-cyano-4-hydroxycinnamic acid as the matrix; electrospray ionization mass spectra (ESI-MS) was recorded using a Micromass Quattro II Electronic HPLC/MS/MS mass spectrometer. HPLC analyses were performed on a Varian Prepstar system for analysis and preparation (Varian Instruments Inc., USA) using a reverse phase HPLC column (Waters, Atlantis C18).

Ultra Performance Liquid Chromatography

HPLC analysis was carried out on a Waters Acquity Peptide Mapping System equipped with a Waters photodiode array detector, a column manager that facilitates 4 column housing, and a sample manager. The instrument is controlled by Empower 2 software. For characterization, calibration and quantitation 45 studies, G5 PAMAM dendrimer, its conjugates, free folic acid (FA) and methotrexate (MTX) were ran on an Acquity BEH C4 column (100×2.1 mm, 1.7 μm). The analysis was carried out using a gradient elution beginning with 99:1 (v/v) water/acetonitrile (ACN) reaching 20:80 water/ACN in 13.40 minutes. The 50 gradient was then reequilibrated back to starting conditions in the next 1.0 minute. Flow rate was maintained at 0.208 mL/min and Trifluoroacetic acid (TFA) at 0.14 wt % concentration was added in water as well as in ACN as a counter ion. A 3 μL of sample was injected using a "partial loop with needle overfill", an inbuilt 55 sample loop option within the software. The column temperature was maintained at 35 C. The concentration of G5 PAMAM dendrimer and dendrimer-ligand conjugate were maintained at 1 mg/mL.

Semi_Prep Reverse Phase High Performance Liquid Chromatography

HPLC isolation was carried out on a Waters Delta 600 HPLC system equipped with a Waters 2996 photodiode array detector, a Waters 2707 auto sampler, and Waters Fraction collector III. The instrument was controlled by Empower 2 software. For purification of the conjugates, an Atlantis Prep T3 column (250×10 mm, 5 μl) was used. The mobile phase for elution of the conjugates was a modified two step linear gradient beginning with 90:10 (v/v) water/ACN and ending with 75:25 (v/v) water/ACN over 20 min at a flow rate of 4.02 mL/min. In the next 10 minutes, gradient was gradually changed to 25:75 (v/v) water/acetonitrile. The system was then reequilibrated back to the starting conditions. TFA at 0.14 wt % concentration in water as well as in ACN was used as a counter ion. The HPLC system is connected to a Waters Fraction Collector III. The fractions of the intended peaks were collected using a time program. The delay time was calculated to be 4 seconds.

Stability Test 15 (100 μM) was incubated with RPMI medium containing final 10% serum. The solution was stirred continuously and maintained at 37° C. for different time periods and the medium proteins were precipitated with 10% DMSO in acetonitrile. The supernatant obtained were subjected HPLC analysis UV absorbance peak area of MTX and FA was used to derive a calibration and used to determine the concentration of released FA and MTX.

Simulation Method

MD simulations were carried out on a G5 PAMAM dendrimer conjugate 15 at neutral solution to investigate structural behaviors of the dendrimer. A molecular structure of G5 PAMAM dendrimer was generated by a recursive script in CHARMM. 73% of the dendrimer surface was acetylated and the rest of the amino groups were protonated. All hydrogens were explicitly included. The MD simulations were carried out using the molecular simulation program CHARMM version 35 (see, e.g., Brooks, B. R.; et al., J. Comp. Chem. 1983, 4, 187-217; herein incorporated by reference in its entirety) and the CHARMM 27 all-atom topology and parameters (see, e.g., MacKerell, A. D.; et al., J. Phys. Chem. B 1998, 102, 3386-3616; herein incorporated by reference in its entirety). The simulations were performed in distance-dependent dielectric constant (D=r) (see, e.g., Pickersgill, R. W. Protein Eng. 1988, 2, 247-248; herein incorporated by reference in its entirety) without non-bonded cutoff distance ($r_c=\infty$), which was proved to be a good simulation condition for non-hydrated PAMAM dendrimer systems (see, e.g., Lee, I.; et al., Macromolecules 2002, 35, 4510-4520; herein incorporated by reference in its entirety). The total potential energy function used in the CHARMM program for MD calculations is described as $$U = U_{bonded} + U_{nonbonded}$$
$$U_{nonbonded} = \sum_{nonbonded} \left\{ \varepsilon \left[ \left(\frac{\sigma}{r_{ij}}\right)^{12} - \left(\frac{\sigma}{r_{ij}}\right)^{6} \right] + \frac{q_i q_j}{D \cdot r_{ij}} \right\}$$

where $\varepsilon$ is the minimum energy of Lennard-Jones potential, $\sigma$ is the distance to give minimum Lennard-Jones potential, q is the partial charge on the atom, D is the dielectric constant, i, j are non-bonded atom pairs and r is the distance between i and j.

After the initial molecular structure was minimized by steepest descent algorithm for 50000 steps and adopted basis Newton-Raphson algorithm for 50000 steps, the system was equilibrated at 300 K for 200 ps, followed by dynamics run for 200 ps. The Verlet algorithm was used with a 1-fs time step in the MD simulations.

Materials

All solvents and chemicals were of reagent grade quality, purchased from Sigma-Aldrich Chemical Co. and used without further purification unless otherwise noted. Thin-layer Chromatography (TLC) and column chromatography were performed with 25 DC-Plastikfolien Kieselgel 60 F254 (Merck), and Baxter silica gel 60 Å (230-400 mesh), respectively.

Synthesis 1-azido-3-aminopropane (see, e.g., Tomalia, et al., Adv Matter 1994 6 529; herein incorporated by reference in its entirety), 3-azido-7-hydroxy-2H-chromen-2-one (see, e.g., Sivakumar et al. (2004) Organic Lett. 6:4603-4606; herein incorporated by reference in its entirety), and tert-butyl 2-(2-(2-aminoethoxy)ethoxy)ethylcarbamate were prepared as reported (see, e.g., Sivakumar et al. (2004) Organic Lett. 6:4603-4606; Carboni et al. (1993) 58:3736-3741; each herein incorporated by reference in its entirety).

N-(3-azidopropyl)-4,6-dichloro-1,3,5-triazin-2-amine (1)

To a solution of cyanuric chloride (18.42 g, 0.10 mol) in acetone (180 mL) in an ice-water bath was added diisopropylethylamine (DIPEA) (12.92 g, 0.10 mol). 1-azido-3-aminopropane (5.00 g, 0.050 mol) in acetone (50 mL) was added slowly over 2 hours. The reaction was stirred at room temperature overnight. The solvent was removed under reduced pressure. The residue was dissolved in $CH_2Cl_2$, washed with water, dried ($Na_2SO_4$) and rotary evaporated. The resulting residue was purified by column chromatography on silica gel (eluent $CH_2Cl_2$) to give 1 as a white solid (5.62 g, 45%): ESI-MS m/z 248.1 (M+H$^+$) calculated for $C_6H_8Cl_2N_7$ 248.0.

2-(4-(3-azidopropylamino)-6-chloro-1,3,5-triazin-2-ylamino)ethanol (2)

Ethanolamine (2.47 g, 40.4 mmol) in acetone (20 mL) was added to a solution of 1 (2.0 g, 8.1 mmol) in acetone (30 mL). The reaction was stirred at room temperature for 24 hours. The acetone was removed by rotary evaporation and the residue was suspended in $CH_2Cl_2$. The mixture was filtered off. The solid collected was washed with $CH_2Cl_2$ with $H_2O$ and dried under reduced pressure to afford 2 as a white solid (1.86 g, 85%). The product is sufficiently pure for further reactions. ESI-MS m/z 273.1 (M+H$^+$) calculated for $C_8H_{14}ClN_8O$ 273.1.

Tert-butyl 2-(2-(4-(3-azidopropylamino)-6-(2-hydroxyethylamino)-1,3,5-triazin-2-ylamino)ethoxy)ethylcarbamate (3)

DIPEA (142 mg, 1.10 mmol), tert-butyl 2-(2-(2-aminoethoxy)ethoxy)ethylcarbamate (273 mg, 1.10 mmol), and 2 (150 mg, 0.55 mmol) were dissolved in THF (5 mL). The mixture was stirred at 70° C. under $N_2$ overnight. The solvent was removed under reduced pressure. The resulting residue was purified by column chromatography on silica gel (eluent $CH_3OH/CH_2Cl_2=2/98$) to give 3 as a white solid (124 mg, 47%): ESI-MS m/z 485.2 (M+H$^+$) calculated for $C_{19}H_{37}N_{10}O_5$ 485.3.

2-(4-(2-(2-aminoethoxy)ethylamino)-6-(3-azidopropylamino)-1,3,5-triazin-2-ylamino)ethanol (4)

(485 mg, 1.0 mmol) was dissolved in $CH_2Cl_2$ (10 mL). TFA (1 mL) was added and the mixture was stirred at room temperature overnight. The solvent was removed under reduced pressure. And the residue was dissolved in $H_2O$ (20 mL) and filtered off. 1N NaOH was added dropwise to the filtrate until the solution became basic. $CH_2Cl_2$ (20 mL) was added and the organic layer was washed with brine and $H_2O$, dried over $Na_2SO_4$, filtered and evaporated under reduced pressure to yield 4 as a white solid (358 mg, 93%): ESI-MS m/z 385.2 (M+H$^+$) calculated for $C_{14}H_{29}N_{10}O_3$ 385.2.

2-(4-(2-(2-aminoethoxy)ethylFA)-6-(3-azidopropylamino)-1,3,5-triazin-2-ylamino)ethanol (5)

2-(4-(2-(2-aminoethoxy)ethylFA)-6-(3-azidopropylamino)-1,3,5-triazin-2-ylamino)ethylMTX (6)

Folic acid (FA) (195 mg, 0.44 mmol) in DMSO (10 mL) was added to a solution of 4 (170 mg, 0.44 mmol) and (DCC) (182 mg, 0.88 mmol) in DMSO (5 mL). The reaction was stirred at room temperature for 24 hours. The reaction mixture was filtered. $H_2O$ (30 mL) was added to the filtrate. The resulting precipitate was filtered, washed with $H_2O$ and acetone, and dried under reduced pressure. The cruder product was further purified by HPLC. Compound 5 was obtained as a yellow solid (147 mg, 41%): ESI-MS m/z 808.3 (M+H$^+$) calculated for $C_{33}H_{46}N_{17}O_8$ 808.4.

Methotrexate (MTX) (25 mg, 0.055 mmol) in DMSO (5 mL) was added to a solution of 5 (40 mg, 0.50 mmol), N,N'-dicyclohexylcarbodiimide (DCC) (204 mg, 1.0 mmol), and trace amount 4-(dimethylamino)pyridine (DMAP) in DMSO (5 mL). The reaction was stirred at room temperature for 24 hours. $H_2O$ (30 mL) was added to the reaction mixture. The solid was collected by centrifugation, washed with $H_2O$ and acetone, and dried under vacuum to yield 6 as a yellow solid.

Two isomers 5 and 6 were isolated and purified as yellow solids, 5 (94 mg 26%), 6 (53 mg, 15%): $^1$H NMR (500 MHz, $d_6$-DMSO) 5 δ 1.23 (m, 1H), 1.77 (m, 2H), 1.85 (m, 1H), 1.96 (m, 1H), 2.26 (m, 2H), 3.49 (m, 25H), 4.35 (m, 1H), 4.50 (s, 1H), 6.63 (d, J=8.5 Hz, 2H), 7.28 (m, 2H), 7.65 (d, J=8.5 Hz, 2H), 7.87-7.98 (m, 2H), 8.10 (m, 1H), 8.27 (m, 1H), 8.66 (s, 1H); 6 δ 1.23 (m, 1H), 1.76 (m, 1H), 1.85 (m, 1H), 2.04 (m, 1H), 2.19 (m, 2H), 3.17 (t, J=6.0 Hz, 1H), 3.35-3.61 (m, 24H), 4.28 (m, 1H), 4.50 (s, 1H), 6.64 (d, J=8.5 Hz, 2H), 7.22 (m, 2H), 7.65 (d, J=8.5 Hz, 2H), 7.89 (m, 1H), 8.11 (m, 1H), 8.19 (d, J=7.5 Hz, 1H), 8.27 (m, 1H), 8.66 (s, 1H); ESI-MS m/z 808.3 (M+H$^+$) calculated for $C_{33}H_{46}N_{17}O_8$ 808.4.

Figure 5:
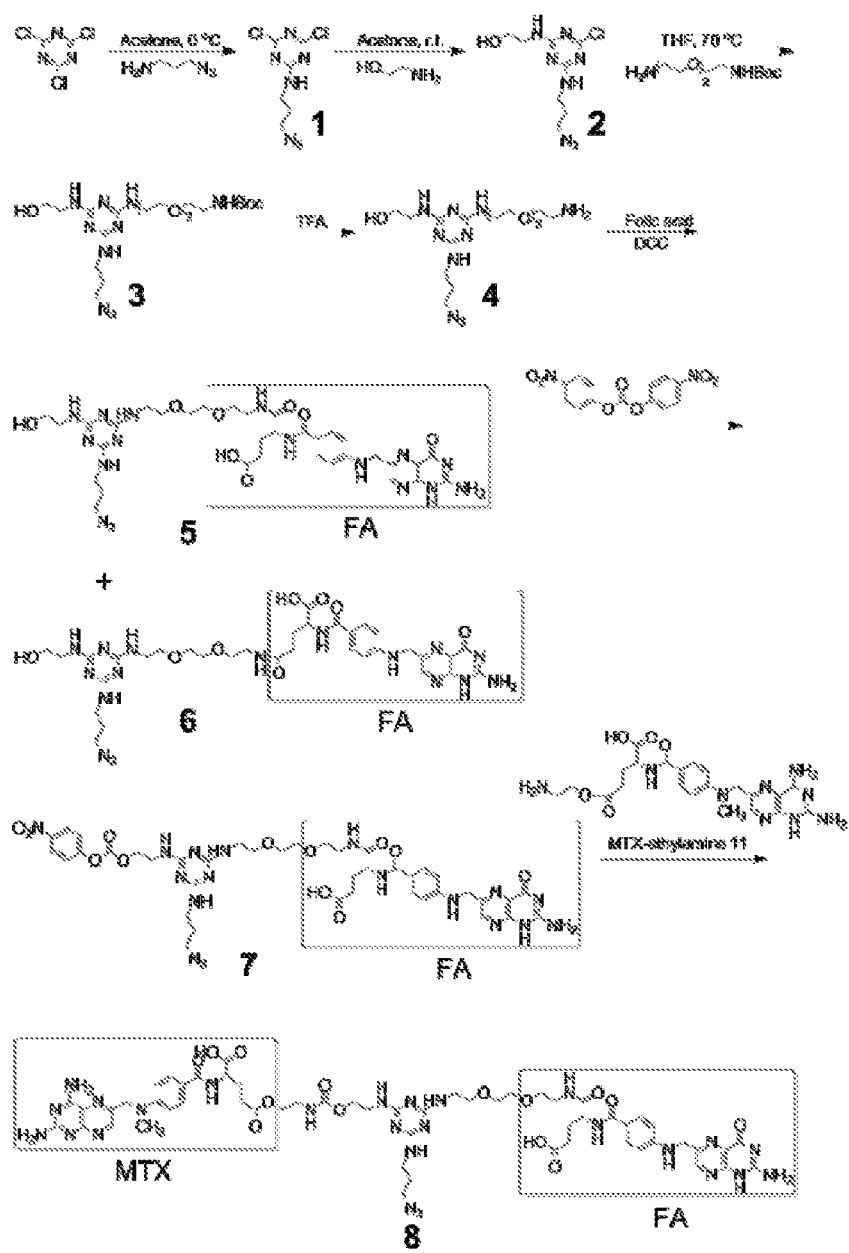
FIG. 5 shows a synthetic scheme of Triazine-$N_3$-γMTX-αFA 8.

(R)-2-(4-((2-amino-4-oxo-1,4-dihydropteridin-6-yl)methylamino)benzamido)-5-(2-(2-(2-aminoethoxy)ethoxy)ethylamino)-5-oxopentanoic acid (7) (see FIG. 5)

Folic acid (882 mg, 2.0 mmol) in DMSO (30 mL) was added to a solution of tert-butyl 2-(2-(2-aminoethoxy)ethoxy)ethylcarbamate (496 mg, 2.0 mmol) and DCC (620 mg, 3.0 mmol) in DMSO (10 mL). The reaction was stirred at room temperature for 24 hours. The reaction mixture was filtered. $H_2O$ (50 mL) was added to the filtrate. The resulting precipitate was filtered, washed with $H_2O$ and acetone, and dried under reduced pressure. The solid collected was suspended in $H_2O$ (30 mL) and TFA (15 mL) was added inside. The mixture was stirred at room temperature overnight, and then filtered. The filtrate was evaporated to dryness under reduced pressure. Compound 7 was obtained as a yellow solid (874 mg, 62%): ESI-MS m/z 572.0 (M+H$^+$) calculated for $C_{25}H_{34}N_9O_8$ 572.3.

3-azido-7-(4,6-dichloro-1,3,5-triazin-2-yloxy)-2H-chromen-2-one (8) (see FIG. 5)

To a solution of cyanuric chloride (2.27 g, 12.3 mmol) in acetone (30 mL) in an ice-water bath was added diisopropylethylamine (DIPEA) (1.59 g, 12.3 mmol). 3-azido-7-hydroxy-2H-chromen-2-one (1.00 g, 4.9 mmol) in acetone (30 mL) was added slowly over 2 hours. The reaction was stirred at room temperature overnight. The solvent was removed under reduced pressure. The residue was dissolved in $CH_2Cl_2$, washed with water, dried ($Na_2SO_4$) and rotary evaporated. The resulting residue was purified by column chromatography on silica gel (eluent $CH_2Cl_2$) to give 8 as a pale yellow solid (1.02 g, 59%): ESI-MS m/z 351.0 (M+H$^+$) calculated for $C_{12}H_5Cl_2N_6O_3$ 351.0.

Figure 6:
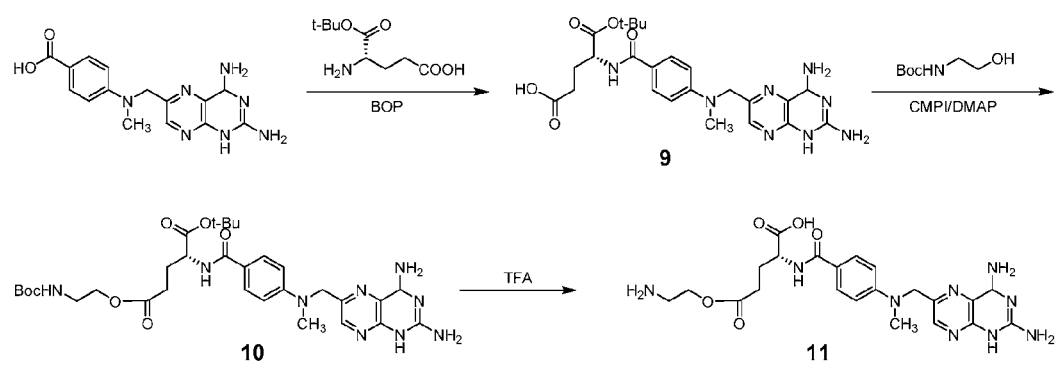
FIG. 6 shows synthesis of γMTX-ethylamine 11.

3-azido-7-(4-chloro-6-(2-hydroxyethylamino)-1,3,5-triazin-2-yloxy)-2H-chromen-2-one (9) (see FIG. 6)

Ethanolamine (45 mg, 0.74 mmol) in acetone (20 mL) was added to a solution of 8 (173 mg, 0.49 mmol) and DIPEA (96 mg, 0.74 mmol) in acetone (10 mL). The reaction was stirred at room temperature for 24 hours. The acetone was removed by rotary evaporation and the residue purified by column chromatography on silica gel (eluent $CH_3OH/CH_2Cl_2=1/99$) to give 9 as a pale yellow solid (144 mg, 78%): ESI-MS m/z 376.1 (M+H$^+$) calculated for $C_{14}H_{11}ClN_7O_4$ 376.1.

7-(4-(2-(2-(2-aminoethoxy)ethoxy)ethylFA)-6-(2-hydroxyethylamino)-1,3,5-triazin-2-yloxy)-3-azido-2H-chromen-2-one (10) (see FIG. 6)

DIPEA (9 mg, 0.07 mmol), 7 (13 mg, 0.02 mmol), and 9 (9 mg, 0.02 mmol) were dissolved in DMSO (2 mL). The mixture was stirred at 60° C. under $N_2$ overnight. The reaction mixture was filtered. $H_2O$ (10 mL) was added to the filtrate. The resulting precipitate was filtered, washed with $H_2O$ and acetone, and dried under reduced pressure. The cruder product was further purified by HPLC. Compound 10 was obtained as a yellow solid: ESI-MS m/z 909.2 (M−H$^+$) calculated for $C_{39}H_{41}N_{16}O_{11}$ 909.3.

Synthesis of (R)-5-(2-(tert-butoxycarbonylamino)ethyl) 1-tert-butyl 2-(4-(((2,4-diaminopteridin-6-yl)methyl)(methyl)amino)benzamido)pentanedioate (MTX-α-OtBu-γ-C$_2$NHBoc) (10) (see FIG. 6)

MTX-α-OtBu 9 (80 mg, 0.16 mmol) in DMF (2 mL) was added to a solution of tert-butyl 2-hydroxyethylcarbamate (38 mg, 0.24 mmol), 2-chloro-1-methyl-pyridinium iodide (CMPI) (44 mg, 0.17 mmol), and 4-(dimethylamino)pyridine (DMAP) (44 mg, 0.36 mmol) in DMF (3 mL). The reaction was stirred at room temperature for 6 hours. The solvent was removed under reduced pressure. The residue was dissolved in $CH_2Cl_2$, washed with water, dried ($Na_2SO_4$) and rotary evaporated. The resulting residue was purified by column chromatography on silica gel (eluent $CH_3OH/CH_2Cl_2=6/94$) to give 10 as a yellow solid (30 mg, 30%): $^1$H NMR (500 MHz, $d_4$-THF) δ 1.38 (s, 9H), 1.45 (s, 9H), 1.88 (m, 1H), 2.21 (m, 1H), 2.39 (m, 2H), 2.54 (s, 2H), 3.19 (s, 3H), 3.25 (m, 2H), 3.93 (m, 1H), 4.12 (m, 1H), 4.66 (m, 1H), 4.75 (s, 2H), 6.43 (t, J=5.5 Hz, 1H), 6.79 (d, J=8.5 Hz, 2H), 7.08 (s, 2H), 7.38 (d, J=8.0 Hz, 1H), 7.74 (d, J=9.0 Hz, 2H), 8.53 (s, 1H), 10.9 (s, 1H); ESI-MS m/z 654.3 (M+H$^+$) calculated for $C_{31}H_{44}N_9O_7$ 654.3.

Synthesis of (R)-5-(2-aminoethoxy)-2-(4-(((2,4-diaminopteridin-6-yl)methyl)(methyl)amino)benzamido)-5-oxopentanoic acid (MTX-α-OtBu-γ-C$_2$H$_2$) (11) (see FIG. 6)

10 (30 mg, 0.046 mmol) was dissolved in 4 mL $CH_2Cl_2$/TFA (1:1) and the mixture was stirred at room temperature for 1 hour. The solvent was removed under reduced pressure. Ether (10 mL) was added to the residue. The solid was collected by centrifugation, washed with H$_2$O and acetone, and dried under vacuum to 3 as a yellow solid (21 mg, 92%). The product is sufficiently pure for further reactions: ESI-MS m/z 496.3 (M–H$^+$) calculated for C$_{22}$H$_{26}$N$_9$O$_5$ 496.2.

Synthesis of 2-(4-(2-(2-aminoethoxy)ethylFA)-6-(3-azidopropylamino)-1,3,5-triazin-2-ylamino)ethyl (4-nitrophenyl) carbonate (Triazine-N$_3$—OC$_6$H$_4$NO$_2$-αFA) (7) (see FIG. 5)

5 (20 mg, 0.025 mmol) was dissolved in DMSO (1 mL), Triethylamine (10 μl) was added to the mixture, followed by bis(4-nitrophenyl)carbonate (15 mg, 0.049 mmol). The mixture was kept at room temperature for 48 h. Ether (10 mL) was added to the residue. The solid was collected by centrifugation, washed with CH$_2$Cl$_2$, methanol, and acetone, and dried under vacuum to give 7 as a yellow solid. The sample was used for the next step without further purification.

Synthesis of 2-(4-(2-(2-aminoethoxy)ethylFA)-6-(3-azidopropylamino)-1,3,5-triazin-2-ylamino)ethylMTX (Triazine-N$_3$-γMTX-αFA) (8) (see FIG. 5)

11 (25 mg, 0.050 mmol) in DMSO (0.5 mL) was added to a solution of 7 and DIPEA (32 mg, 0.25 mmol) in DMSO (0.5 mL). The reaction was stirred at room temperature for 24 hours. Ether (10 mL) was added to the residue. The solid was collected by centrifugation, washed with methanol and acetone, and dried under vacuum. The cruder product was further purified by semi-prep. HPLC to yield 8 as yellow solids (12 mg, 36%): $^1$H NMR (500 MHz, d$_6$-DMSO) δ 1.74 (m, 2H), 1.83 (m, 1H), 1.95 (m, 2H), 2.08 (m, 2H), 2.17 (m, 2H), 2.39 (m, 3H), 3.07-3.46 (m, 28H), 3.95-4.03 (m, 2H), 4.18-4.25 (m, 2H), 4.31 (m, 2H), 4.48 (m, 2H), 4.78 (m, 2H), 6.62 (m, 4H), 6.82 (m, 3H), 6.95 (m, 1H), 7.22 (m, 1H), 7.46 (m, 2H), 7.62-7.73 (m, 5H), 7.86 (m, 1H), 7.97 (m, 1H), 8.56 (s, 1H), 8.63 (s, 1H); ESI-MS m/z 664.3 (M–2H$^+$)/2 calculated for (C$_{56}$H$_{70}$N$_{26}$O$_{14}$-2H$^+$)/2 664.3.

Figure 7:
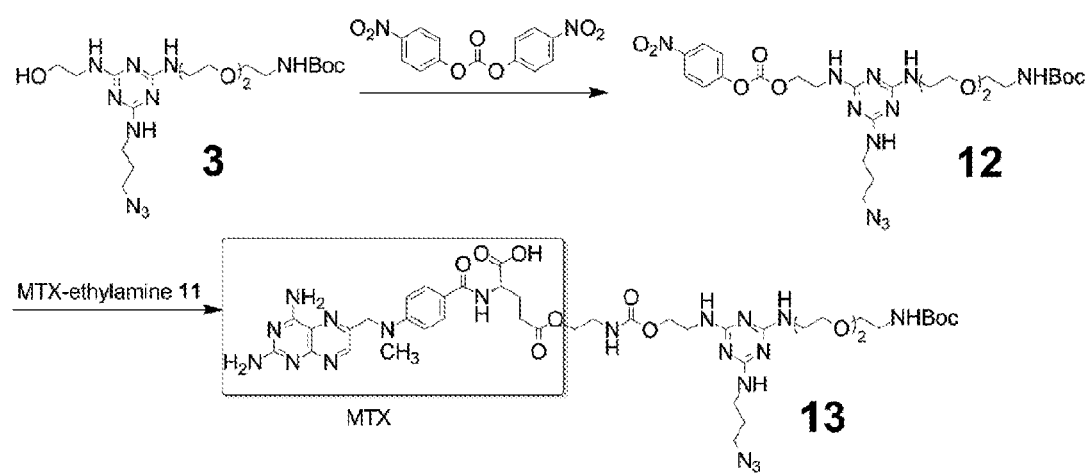
FIG. 7 shows a synthetic scheme of Triazine-$N_3$-γMTX-NHBoc 13.

Synthesis of tert-butyl (2-(2-(2-((4-((3-azidopropyl)amino)-6-((2-(((4-nitrophenoxy)carbonyl)oxy)ethyl)amino)-1,3,5-triazin-2-yl)amino)ethoxy)ethoxy)ethyl)carbamate (Triazine-N$_3$—OC$_6$H$_4$NO$_2$—NHBoc) (12) (see FIG. 7)

3 (158 mg, 0.33 mmol) was dissolved in DMF (3 mL). Triethylamine (200 μA) was added to the mixture, followed by bis(4-nitrophenyl)carbonate (198 mg, 0.65 mmol). The mixture was kept at room temperature for 24 h. The solvent was removed under reduced pressure. The resulting residue was purified by column chromatography on silica gel (eluent CH$_3$OH/CH$_2$Cl$_2$=5/95) to give 12 as a white solid (182 mg, 86%): $^1$H NMR (500 MHz, CDCl$_3$) δ 1.45 (s, 9H), 1.84 (m, 2H), 2.17 (s, 1H), 3.32-3.77 (m, 18H), 4.42 (m, 2H), 5.25 (m, 1H), 5.94 (m, 1H), 6.30-6.48 (m, 1H), 7.37 (d, J=9.0 Hz, 2H), 8.27 (d, J=8.5 Hz, 2H); ESI-MS m/z 650.2 (M+H$^+$) calculated for C$_{26}$H$_{40}$N$_{11}$O$_9$ 650.3.

Synthesis of 2-(4-(2-(2-aminoethoxy)ethoxy)ethyl) carbamate)-6-(3-azidopropylamino)-1,3,5-triazin-2-ylamino)ethylMTX (Triazine-N$_3$-MTX-NHBoc) (13) (see FIG. 7)

11 (10 mg, 0.020 mmol) in DMF (0.5 mL) was added to a solution of 12 (26 mg, 0.040 mmol) and DIPEA (26 mg, 0.20 mmol) in DMF (0.5 mL). The reaction was stirred at room temperature for 24 hours. CH$_2$Cl$_2$ (5 mL) was added to the residue. The solid was collected by centrifugation, washed with acetone and CH$_2$Cl$_2$, and dried under vacuum to give 13 as a yellow solid (7 mg, 35%). The sample was used for the next step without further purification: ESI-MS m/z 1006.5 (M+H$^+$) calculated for (C$_{56}$H$_{70}$N$_{26}$O$_{14}$C$_{33}$H$_{46}$N$_{17}$O$_8$+H$^+$) 1006.5.

General Procedure for Synthesis of Dendrimer Conjugates

Figure 8:
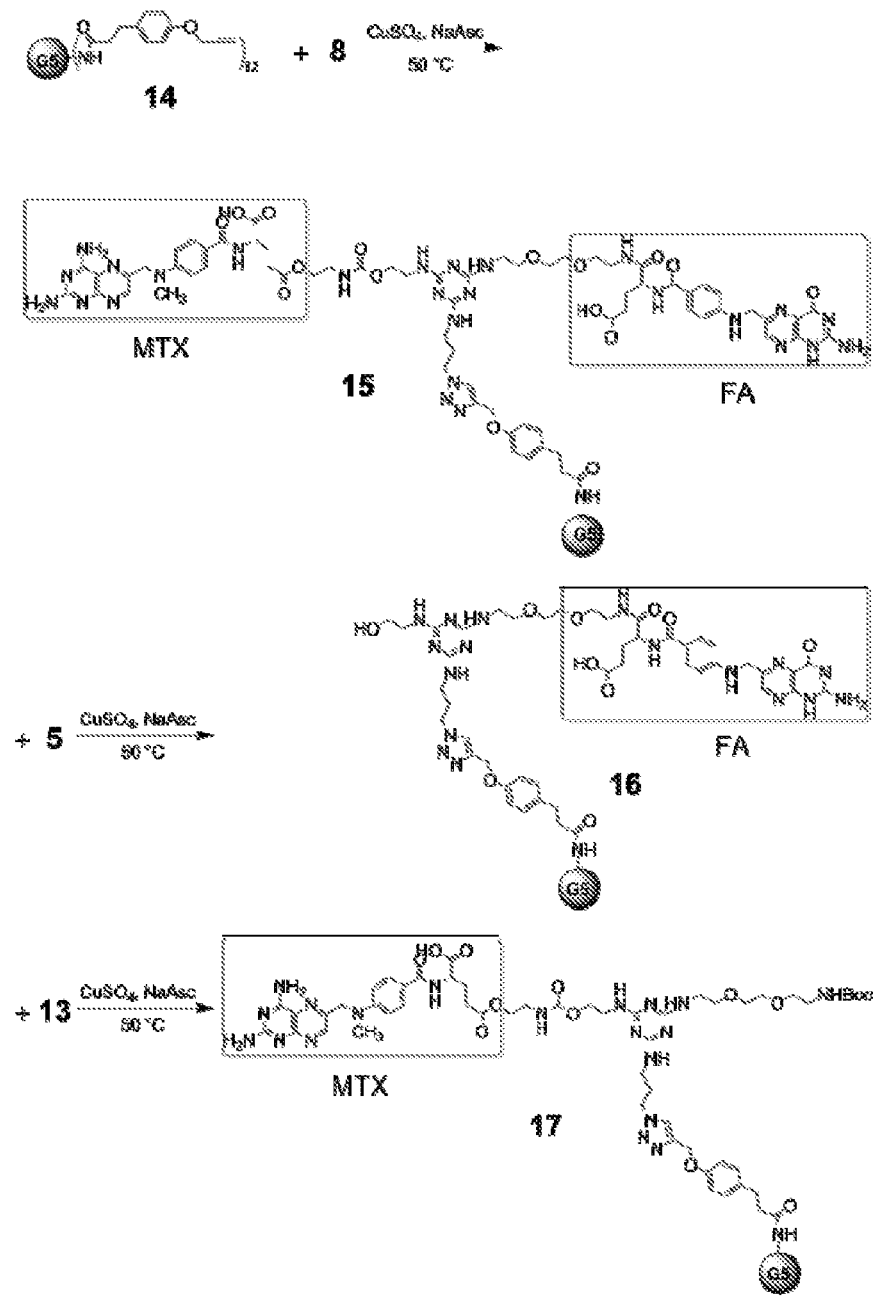
FIG. 8 shows synthesis of dendrimer conjugates G5-Triazine-γMTX-αFA 15, G5-Triazine-αFA 16, and G5-Triazine-γMTX 17.

Synthesis of G5-NHAc$_{80}$-Alkyne$_{12}$ (14) (see FIG. 8)

Compound was synthesized according to the literature.[7] G5-NHAc$_{80}$-Alkyne$_{12}$ 14 White solid: MALDI-TOF mass 32774. The $^1$H NMR integration determined the mean number of Acetyl groups per dendrimer is 80.1. The mean number of Alkyne ligands per dendrimer is 12.3.
$^1$H NMR Analyses to Determine the Degree of Functionalization
The number of ligands that attached to the dendrimer were determined by comparing the integration of the methyl protons of the terminal acetyl groups to the aromatic protons on the conjugated ligands (see, e.g., Mullen, D. G.; Acs Nano 2010, 4, 657-670; herein incorporated by reference in its entirety). The number of acetyl groups per dendrimer was independently determined by first computing the total number of end groups from the number average molecular weight (GPC) and potentiometric titration data for G5-NH$_2$(100%) as previously described (see, e.g., Majoros, I. J.; et al., J Med Chem 2005, 48, 5892-5899; herein incorporated by reference in its entirety). The total number of end groups was applied to the ratio of primary amines to acetyl groups, obtained from the $^1$H NMR of the partially acetylated dendrimer, to compute the average number of acetyl groups per dendrimer.
General Procedure for Cu(I) Catalyzed Cycloaddition
G5-NHAc$_{80}$-Alkyne$_{12}$ 14 (see FIG. 8) (14 mg, 0.43 μmol) was dissolved in Cu(II) sulfate (10 mol % per triazine-azide, 1 mg/mL H$_2$O) and sodium ascorbate (60 mol % per triazine-azide, 1 mg/mL H$_2$O solution) solution. The Triazine-azide substrates (5, 8, and 13), (7.5 azide mole ratio to G5-NHAc$_{80}$-Alkyne$_{12}$, 10 mg/mL DMSO solution) were added. The reaction mixture was heated in an oil bath at 50° C. overnight. Samples were purified using 10 000 MWCO centrifugal filtration devices. Purification consisted of ten cycles (20 min at 4800 rpm) using PBS (5 cycles) and DI water (5 cycles). The purified dendrimer samples were lyophilized to yield 15, 16, and 17 (FIG. 8) as yellow solids.
G5-Triazine-γMTX$_{3.1}$-αFA$_{3.1}$ 15 (FIG. 8): MALDI-TOF mass 35094. The $^1$H NMR integration determined the mean number of Triazine-γMTX-αFA attached is 3.1.
G5-Triazine-OH-αFA$_{4.2}$ 16 (FIG. 8): MALDI-TOF mass 33059. The $^1$H NMR integration determined the mean number of Triazine-OH-αFA is 4.2. G5-Triazine-γMTX$_{3.7}$-NHBoc 17 (FIG. 8): MALDI-TOF mass 34266. The $^1$H NMR integration determined the mean number of Triazine-γMTX-NHBoc is 3.7.

Example III

This example describes the synthesis of triazine derivatives, their conjugation to PAMAM dendrimers, and in vitro cytotoxicity studies on FR-expressing KB cells using these dendrimer conjugates.
Trifunctional triazine derivatives were synthesized from cyanuric chloride by consecutive aromatic nucleophilic substitution reactions, which were controlled by temperature to run in a stepwise manner (FIG. 5). Folic acid (FA) was conjugated to the triazine through an amide bond. An ester bond was chosen for methodtrexate (MTX) conjugation with expectation for improved release of drug. The monosubstituted triazine Triazine-N$_3$ 1 was synthesized by adding 3-azidopropan-1-amine to a solution of cyanuric chloride in acetone at 0° C. The second substitution was carried out in the same solvent at room temperature with 2-aminoethanol. The bisubstituted Triazine-$N_3$—OH 2 was treated with tert-butyl (2-(2-(2-aminoethoxy)ethoxy)ethyl)carbamate in the presence of diisopropylethylamine (DIPEA) in tetrahydrofuran (THF) at 70° C. to form Trazine-$N_3$—OH—NHBoc 3 containing a primary amine in a protected form, which was used for conjugation with FA. Reaction of 2 with unprotected 2,2'-(ethane-1,2-diylbis(oxy))diethanamine had a poor yield due to a major by-product of the triazine dimer. After removal of the BOC protecting group, FA was coupled to Triazine-$N_3$—OH—$NH_2$ 4 by N,N'-Dicyclohexylcarbodiimide (DCC) in dimethylsulfoxide (DMSO). This sample was purified on RP-HPLC. Two isomers, 5 and γ-carboxyl 6 group linked products were separated and purified, and relatively higher (60%) α-carboxyl linked product was obtained vs. γ isomer (40%), based on HPLC analysis. Both isomers were conjugated to PAMAM dendrimers. Resulting conjugates showed similar binding affinities to purified FR-α in a surface plasmon resonance (SPR)-based binding study. This finding was consistent with other research group's results (see, e.g., Leamon, C. P.; et al., J Drug Target 1999, 7, 157; Bettio, A.; et al., each incorporated by reference in their entireties). The HPLC-purified α-carboxyl group linked isomer 5 was used for further studies due to its relatively higher yield.

The strategy for the synthesis of trifunctional Triazine-$N_3$-γMTX-αFA 8 was first approached by direct coupling MTX with Triazine-$N_3$—OH-αFA 5 using DCC/4-(dimethylamino)pyridine (DMAP) or DCC/4-pyrrolidinopyridine (see, e.g., Devineni, D.; et al., Bioconjugate Chem 1995, 6, 203; herein incorporated by reference in its entirety). However, both reactions were unsuccessful due to very low yield. To solve this problem, an alternate synthetic route was chosen (FIG. 5). The hydroxyl group of 5 was first activated with bis(4-nitrophenyl)carbonate to provide carbonate 7. Then carbonate 7 was treated with γMTX-ethylamine 11 (FIG. 6) to form the target compound Triazine-$N_3$-γMTX-αFA 8. Control sample Triazine-$N_3$-γMTX-NHBoc 13 was synthesized in a similar manner (FIG. 7).

γMTX-ethylamine 11 was synthesized following the literature (see, e.g., Nagy, A.; et al., P Natl Acad Sci USA 1993, 90, 6373; herein incorporated by reference in its entirety). In brief, (benzotriazol-1-yloxytris(dimethylamino) phosphonium hexafluorophosphate) (BOP) activated 4-amino-4-deoxy-$N^{10}$-methyl pteroic acid (APA) in DMSO was reacted with the potassium salt of glutamic acid α-tert-butyl ester to form the α-carboxyl protected MTX derivative. The selectively protected MTX derivative was then coupled to tert-butyl (2-hydroxyethyl)carbamate by 2-chloro-1-methyl-pyridinium iodide (CMPI)/DMAP. The t-butyl and BOC protecting groups were then removed by trifluoroacetic acid (TFA) at the same time to afford the γMTX-ethylamine 11. Alkyne-terminated generation 5 (G5) PAMAM dendrimer G5-NHAc-Alkyne 14 has been previously synthesized (see, e.g., Mullen, D. G.; et al., Acs Nano 2010, 4, 657; herein incorporated by reference in its entirety). Partially acetylated dendrimers was employed in this study because these materials have been shown to be most effective for targeted drug delivery applications (see, e.g., Thomas, T. P.; et al., J Med Chem 2005, 48, 3729; Kukowska-Latallo, J. F.; et al., Cancer Res 2005, 65, 5317; each herein incorporated by reference in their entireties). The parent amine-terminated materials have been shown to non-selectively cause cell membrane permeability and are not suited for in vivo targeted drug delivery applications.[31-33] Target conjugate G5-Triazine-γMTX-αFA 15, control samples G5-Triazine-OH-αFA 16, and G5-Triazine-γMTX-NHBoc 17 were synthesized by one step "click" reaction to the G5-Ac-Alkyne 14 with corresponding triazine derivatives (FIG. 8). MALDI-TOF and NMR analyses were performed to determine the degree of functionalization.

The cytotoxicity of the newly synthesized G5-Triazine-γMTX-αFA 15 was determined in vitro by the XTT assay in KB cells, which express a high cell surface FR (FIG. 9). The cytotoxicity with another batch of G5-FA-MTX synthesized by Cambrex Inc. was also compared, using the classic sequential conjugation synthetic pathway (see, e.g., Majoros, I. J.; et al., J Med Chem 2005, 48, 5892; herein incorporated by reference in its entirety). Previous studies have shown that this batch of Cambrex conjugates was cytotoxic in vitro and tumoricidal in vivo, with potency similar to that of our previously published compound (see, e.g., Thomas, T. P.; et al., J Med Chem 2005, 48, 3729; Kukowska-Latallo, J. F.; et al., Cancer Res 2005, 65, 5317; each herein incorporated by reference in their entireties). The newly synthesized G5-Triazine-γMTX-αFA 15 inhibited the KB cell growth in a dose-dependence fashion, with increased cytotoxic potential vs. the Cambrex batch. The G5-Triazine-γMTX-αFA 15 and the Cambrex conjugate inhibited cells growth with IC50 of ~5 and 20 nM, respectively. The Cambrex conjugate has 4-5 FA and 7-8 MTX per dendrimer, while 15 has 3.1 each of the FA and MTX per dendrimer. Despite the increased MTX content on the Cambrex conjugate, 15 carried higher cytotoxic potential. As MTX has ~1000× fold more affinity toward dihydrofolate reductase (DHFR) vs. FA, it is possible that the close molecular proximity of the FA and MTX on 15, but not on the Cambrex conjugate, may allow the preferential binding of MTX on 15 as it is being juxtaposed at the DHFR binding site. The control conjugate G5-Triazine-γMTX 17 without the targeting moiety FA also showed a dose dependent cytotoxicity, though with a much higher IC50 (~75 nM) vs. G5-Triazine-γMTX-αFA 15. As the G5-Triazine-γMTX conjugate is unlikely to be taken up through the reduced folate carrier (RFC) due to size constraints of this membrane channel, it is possible that it is internalized into the cells through polyvalent binding through the FR.

In order to confirm that the observed cytotoxicity was not due to free MTX released from the conjugate during incubation in the cell culture medium, the stability of the dendrimer conjugate was tested in the cell culture medium. For this analysis, the G5-Triazine-γMTX-αFA 15 was incubated with cell culture medium for 1, 4, 24, and 72 h. During the 72 h incubation time periods, both FA and MTX showed a slow release in a time-dependent fashion (FIG. 10). Amide-linked FA was quite stable against hydrolytic cleavage, whereas the ester-linked MTX was more liable to hydrolysis, 1.0% FA vs. 4.6% MTX, for the 72 h period studied. This data shows that the major antiproliferative effect of the G5-Triazine-γMTX-αFA 15 was not the result of free MTX.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in dendrimer synthesis, drug delivery, or related fields are intended to be within the scope of the following claims.

We claim:

1. A composition comprising a PAMAM dendrimer conjugated with a triazine compound, wherein said triazine compound is selected from the group consisting of

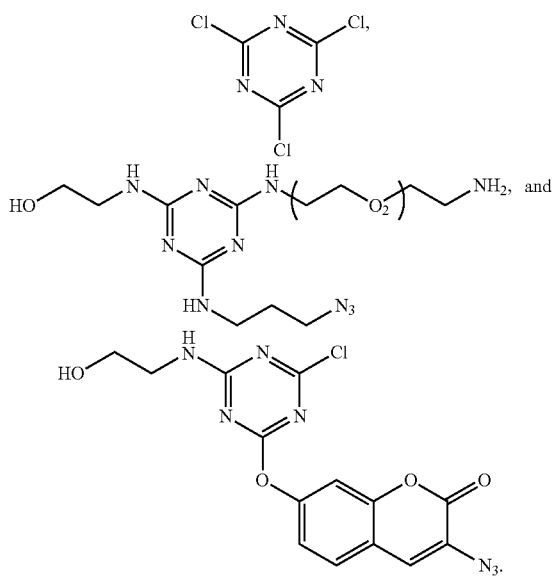

2. The composition of claim 1, wherein said PAMAM dendrimer is conjugated with said triazine compound via a 3-azido-coumarine linkage agent.

3. The composition of claim 1, wherein said triazine compound is conjugated with one or more ligands.

4. The composition of claim 3, wherein said one or more ligands are independently selected from the group consisting of a therapeutic agent, a targeting agent, an imaging agent, and a trigger agent.

5. The composition of claim 3, wherein said one or more ligands are methotrexate, folic acid, and 3-azido-coumarine.

6. A method of synthesizing a functionalized dendrimer, said method comprising:

a) providing an alkyne-modified PAMAM dendrimer and a triazine compound, wherein said triazine compound is selected from the group consisting of

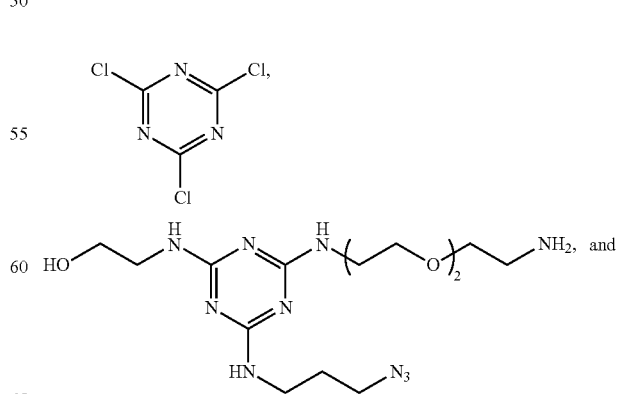

-continued

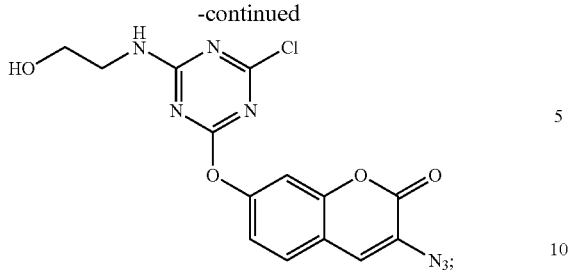

and
b) conjugating said alkyne-modified PAMAM dendrimer with said triazine compound.

7. The method of claim 6, wherein conjugating of said alkyne-modified PAMAM dendrimer with said triazine compound occurs via a click chemistry reaction.

8. The method of claim 6, wherein said PAMAM dendrimer is conjugated with said triazine compound via a 3-azido-coumarine linkage agent.

9. The method of claim 6, further comprising step c) conjugating one or more ligands with said triazine compound.

10. The method of claim 9, wherein said one or more ligands are selected from the group consisting of a therapeutic agent, a targeting agent, an imaging agent, and a trigger agent.

11. The method of claim 9, wherein said one or more ligands are methotrexate and folic acid.

* * * * *

SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position is linked to a
      (7-methoxycoumarin-4-yl)acetyl
<220> FEATURE:
<221> NAME/KEY: MISC_FEATURE
<222> LOCATION: (7)..(7)
<223> OTHER INFORMATION: The residue at this position is linked to a
      2,4-dinitrophenyl group and NH2

<400> SEQUENCE: 1

Tyr Glu Val Asp Gly Trp Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

His Leu Asn Ile Leu Ser Thr Leu Trp Lys Tyr Arg
1               5                   10